(12) United States Patent
Hagooly et al.

(10) Patent No.: US 10,844,036 B2
(45) Date of Patent: Nov. 24, 2020

(54) PROCESSES FOR OBTAINING PURIFIED UNSATURATED MACROCYCLIC COMPOUNDS

(71) Applicant: Agan Aroma & fine chemicals Ltd., Ashdod (IL)

(72) Inventors: Youlia Hagooly, Tel-Aviv (IL); Alexander Laskavy, Netanya (IL); Tehila Yosef Gerufi, Yad Binyamin (IL); Eyal Ben-Ari, Yavne (IL)

(73) Assignee: Agan Aroma & fine chemicals Ltd., Ashdod (IL)

( * ) Notice: Subject to any disclaimer, the term of this patent is extended or adjusted under 35 U.S.C. 154(b) by 0 days.

(21) Appl. No.: 16/466,643

(22) PCT Filed: Dec. 5, 2017

(86) PCT No.: PCT/IB2017/057646
§ 371 (c)(1),
(2) Date: Jun. 5, 2019

(87) PCT Pub. No.: WO2018/104856
PCT Pub. Date: Jun. 14, 2018

(65) Prior Publication Data
US 2019/0345128 A1 Nov. 14, 2019

Related U.S. Application Data

(60) Provisional application No. 62/429,919, filed on Dec. 5, 2016.

(51) Int. Cl.
| | | |
|---|---|---|
| *C07D 313/00* | (2006.01) | |
| *B01J 39/05* | (2017.01) | |
| *B01J 49/40* | (2017.01) | |
| *B01J 49/06* | (2017.01) | |
| *B01D 15/18* | (2006.01) | |
| *B01D 15/36* | (2006.01) | |
| *B01J 39/20* | (2006.01) | |
| *B01J 47/02* | (2017.01) | |
| *C07B 63/00* | (2006.01) | |

(52) U.S. Cl.
CPC .......... *C07D 313/00* (2013.01); *B01D 15/185* (2013.01); *B01D 15/362* (2013.01); *B01J 39/05* (2017.01); *B01J 39/20* (2013.01); *B01J 47/02* (2013.01); *B01J 49/06* (2017.01); *B01J 49/40* (2017.01); *C07B 63/00* (2013.01)

(58) Field of Classification Search
CPC ................................................... C07D 313/00
USPC ....................................................... 549/266
See application file for complete search history.

(56) References Cited

U.S. PATENT DOCUMENTS

| | | | |
|---|---|---|---|
| 3,600,453 A | 8/1971 | Reichenbacher et al. | |
| 4,960,882 A * | 10/1990 | Bradshaw | C07D 498/08 540/468 |
| 5,321,193 A * | 6/1994 | Lin | B01J 21/02 502/355 |
| 7,211,703 B2 * | 5/2007 | Chiang | C07C 29/76 568/913 |

FOREIGN PATENT DOCUMENTS

| | | |
|---|---|---|
| CN | 1192382 | 9/1998 |
| EP | 1845078 | 10/2007 |
| WO | WO 2006/116419 | 11/2006 |
| WO | WO 2015/107017 | 7/2015 |
| WO | WO 2015/136093 | 9/2015 |
| WO | WO 2018/104856 | 6/2018 |

OTHER PUBLICATIONS

Beek, Phytochemical Analysis. vol. 6, 1-19 (1995).*
Adlof, Journol of Chromatography A, 659 (1994) 9S-99.*
Damyanova, Journal of Chromatography A, 693 (1995) 235-239).*
Corrected International Search Report and the Written Opinion dated Mar. 29, 2018 From the International Searching Authority Re. Application No. PCT/IB2017/057646. (13 Pages).
International Preliminary Report on Patentability dated Jun. 20, 2019 From the International Bureau of WIPO Re. Application No. PCT/IB2017/057646. (7 Pages).
International Search Report and the Written Opinion dated Mar. 29, 2018 From the International Searching Authority Re. Application No. PCT/IB2017/057646. (13 Pages).
Hagiwara et al. "Expedient Synthesis of (E)-3-Methylcyclopentadec-2-En-1-One, An Important Precursor for (R)-(-)Muscones", Falvour and Fragrance Journal, 27(1): 54-59, Published Online Jul. 25, 2011. (R)-(-)Muscones.
Wei et al. "A Highly Convergent and Efficient Synthesis of a Macrocyclic Hepatitis C Virus Protease Inhibitor B1 201302", Organic Letters, 15(6): 1016-1019, Published on Web Feb. 13, 2013. The Compound B1 201302.
Supplementary European Search Report and the European Search Opinion dated Jul. 14, 2020 From the European Patent Office Re. Application No. 17878682.8. (9 Pages).

* cited by examiner

*Primary Examiner* — Nizal S Chandrakumar

(57) ABSTRACT

A process of obtaining a purified geometric isomer of an unsaturated macrocyclic compound is disclosed herein. The process is effected by contacting an ion exchange medium comprising silver ions with a mixture comprising at least one geometric isomer of the unsaturated macrocyclic compound, to thereby obtain at least one fraction comprising the purified geometric isomer of the macrocyclic compound. A system configured for performing the process is also disclosed.

25 Claims, 2 Drawing Sheets

PROCESSES FOR OBTAINING PURIFIED UNSATURATED MACROCYCLIC COMPOUNDS

RELATED APPLICATIONS

This application is a National Phase of PCT Patent Application No. PCT/IB2017/057646 having International filing date of Dec. 5, 2017, which claims the benefit of priority under 35 USC § 119(e) of U.S. Provisional Patent Application No. 62/429,919 filed on Dec. 5, 2016. The contents of the above applications are all incorporated by reference as if fully set forth herein in their entirety.

FIELD AND BACKGROUND OF THE INVENTION

The present invention, in some embodiments thereof, relates to manufacturing of chemicals, and more particularly, but not exclusively, to processes of obtaining purified macrocyclic compounds and to systems designed for performing such processes.

Musk refers to a variety of compounds with similar odors, commonly used as base notes in perfumery. Musk compounds can be divided into three major classes: nitro arenes, polycyclic benzene derivatives, and macrocyclic compounds [Kraft et al., *Angew Chem Int Ed* 2000, 39:2980-3010]. Macrocyclic musk compounds, which include naturally occurring musk compounds, are more biodegradable than nitro arenes and polycyclic musk compounds, and cause less ecological concerns.

Commercially important musk compounds which are naturally occurring include cyclopentadecanone, which is produced by muskrats; muscone (3-methyl-cyclopentadecan-1-one), the R enantiomer of which is produced by musk deer; cis-civetone ((9Z)-cycloheptadec-9-en-1-one), which is produced by civets; 15-pentadecanolide, which is present in angelica root oil; and cis-ambrettolide ((10Z)-oxacycloheptadec-8-en-2-one), which is present in ambrette seed oil. Naturally occurring macrocyclic musk compounds are often prepared synthetically, as are a variety of structurally similar macrocyclic musk compounds which are not known to occur in nature.

Some musk compounds have double bonds which exhibit a cis/trans stereoisomerism which affects odor, which lends importance to the ability to separate cis and trans isomers. For example, the odor of (5Z)-3-methylcyclopentadec-5-en-1-one is described as muskier, more elegant and less animal than that of (5E)-3-methylcyclopentadec-5-en-1-one; whereas (4Z)-3-methylcyclopentadec-4-en-1-one is almost odorless, in contrast to the musky odor of (4E)-3-methylcyclopentadec-4-en-1-one. For cycloheptadec-9-en-1-one (civetone), oxacycloheptadec-8-en-2-one (ambrettolide) and cyclopentadec-4-en-1-one (exaltenone), the cis (Z) isomer is most commonly used as musk, whereas the trans (E) isomer of oxacycloheptadec-10-en-2-one (iso-ambrettolide) is the commonly used isomer (e.g., under the tradename Ambrettolide®).

Stereoselective syntheses of macrocyclic alkenes have been described based on a chiral starting material such as phloionolic acid [Sanz & Seoane, *J Chem Soc Perkins Trans I* 1982, 1837-1839], or on Lindlar reduction of alkynes to cis-alkenes [Furstner & Seidel, *J Organometal Chem* 2000, 606:75-78; Hagiwara et al., *Nat Product Comm* 2012, 7:913-915].

Hagiwara et al. [*Flavour Fragr J* 2012, 27:54-59] describes selective preparation of the E isomer of 3-methylcyclopentadec-2-en-1-one for use in preparing (R)-muscone by catalytic asymmetric hydrogenation.

Morris [*J Lipid Res* 1966, 7:717-732] provides a review of separations of lipids by silver ion chromatography based on the number, type and position of unsaturated centers they contain, and describes a separation of cis and trans 5-cyclodecenols using a column of silica gel impregnated with aqueous silver nitrate.

International Patent Application Publication WO 2006/116419 describes separation of E and Z isomers of an alkene alcohol, such as hexenol, or derivative thereof, by continuously contacting an ion exchange medium with silver and/or copper ions with a feed stream comprising the E and Z isomers of the alkene alcohol or derivative thereof.

Additional background art includes U.S. Pat. No. 5,354,735; International Patent Application Publication WO 2015/136093; Moore ["Synthesis and Fragrance Properties of Macrocyclic Musks", www(dot)chemistry(dot)Illinois(dot)edu/research/organic/seminar_extracts/2004_2005/12_Moor e_Abstract_SP05.pdf]; Hamasaki et al. [*Tetrahedron* 2000, 56:7423-7425]; Ruedi et al. [*Org Lett* 2004, 6:2989-2991]; and Zou et al. [*Chem Eur J* 2012, 18:7010-7015].

SUMMARY OF THE INVENTION

According to an aspect of some embodiments of the invention, there is provided a process of obtaining a purified geometric isomer of an unsaturated macrocyclic compound, the process comprising contacting an ion exchange medium comprising silver ions with a mixture comprising at least one geometric isomer of the unsaturated macrocyclic compound, to thereby obtain at least one fraction comprising the purified geometric isomer of the macrocyclic compound.

According to an aspect of some embodiments of the invention, there is provided a purified macrocyclic compound obtainable according to the process described herein.

According to an aspect of some embodiments of the invention, there is provided a system comprising an ion exchange medium which comprises silver ions, the system being configured for obtaining a purified geometric isomer of an unsaturated macrocyclic compound according to the process described herein.

According to some embodiments of any of the embodiments of the invention, the purified geometric isomer is characterized by a purity of at least 90%.

According to some embodiments of any of the embodiments of the invention, the mixture comprises a first geometric isomer and a second geometric isomer of the unsaturated macrocyclic compound, and the process comprises separating the first geometric isomer and the second geometric isomer, the purified geometric isomer being a purified first geometric isomer.

According to some embodiments of any of the embodiments of the invention, a concentration ratio of the first geometric isomer to the second geometric isomer in the purified first geometric isomer is at least 150% of a concentration ratio of the first geometric isomer to the second geometric isomer in the mixture.

According to some embodiments of any of the embodiments of the invention, the mixture comprises an additional compound in combination with the unsaturated macrocyclic compound, and the process comprises separating the additional compound from the unsaturated macrocyclic compound.

According to some embodiments of any of the embodiments of the invention, the additional compound comprises an additional macrocyclic compound.

According to some embodiments of any of the embodiments of the invention, a percentage of the additional compound by weight of the total weight of the additional compound and the geometric isomer in the purified geometric isomer is at least 25% less than a percentage of the additional compound by weight of the total weight of the additional compound and the geometric isomer in the mixture.

According to some embodiments of any of the embodiments of the invention, at least 60% of the cations of the ion exchange medium are silver ions.

According to some embodiments of any of the embodiments of the invention, a concentration of silver ions in the ion exchange medium is at least 20% by weight of the total dry weight of the ion exchange medium.

According to some embodiments of any of the embodiments of the invention, at least 85% of the cations of the ion exchange medium are silver ions.

According to some embodiments of any of the embodiments of the invention, a concentration of silver ions in the ion exchange medium is at least 30% by weight of the total dry weight of the ion exchange medium.

According to some embodiments of any of the embodiments of the invention, a concentration of silver ions in the ion exchange medium is in a range of from 0.1 to 0.3 grams silver ions per cm$^3$.

According to some embodiments of any of the embodiments of the invention, the ion exchange medium comprises cross-linked polystyrene substituted with sulfonic acid groups or a salt thereof.

According to some embodiments of any of the embodiments of the invention, the process further comprises contacting the ion exchange medium comprising silver ions with an alcoholic and/or aqueous solvent.

According to some embodiments of any of the embodiments of the invention, the solvent comprises methanol and/or ethanol.

According to some embodiments of any of the embodiments of the invention, a concentration of water in the solvent is in a range of from 0 to 40 weight percents.

According to some embodiments of any of the embodiments of the invention, a concentration of water in the solvent is in a range of from 20 to 40 weight percents.

According to some embodiments of any of the embodiments of the invention, the solvent is contacted with the ion exchange medium such that it flows through the ion exchange medium at a rate in a range of from 1 to 10 bed volumes per hour.

According to some embodiments of any of the embodiments of the invention, the solvent is contacted with the ion exchange medium such that it flows through the ion exchange medium at a rate in a range of from 2.5 to 250 cm per minute.

According to some embodiments of any of the embodiments of the invention, contacting the ion exchange medium with the mixture is effected at a temperature in a range of from 20° C. to 80° C.

According to some embodiments of any of the embodiments of the invention, contacting the ion exchange medium with the mixture is effected at a first temperature, and the process further comprises eluting the at least one fraction from the ion exchange medium at a second temperature, the second temperature being higher than the first temperature.

According to some embodiments of any of the embodiments of the invention, the process comprises:

contacting the ion exchange medium comprising silver ions with the mixture comprising at least one geometric isomer of the unsaturated macrocyclic compound, to thereby obtain at least one first fraction comprising the purified geometric isomer, and at least one second fraction comprising the geometric isomer at a purity which is lower than a purity of the geometric isomer in the mixture; and contacting an ion exchange medium comprising silver ions with at least one second fraction, to thereby obtain at least one third fraction comprising the purified geometric isomer.

According to some embodiments of any of the embodiments of the invention, the process comprises increasing an isomeric purity of the geometric isomer in at least one second fraction, to thereby obtain at least one second fraction having an increased isomeric purity, and contacting an ion exchange medium comprising silver ions with the at least one second fraction having an increased isomeric purity, to thereby obtain the at least one third fraction.

According to some embodiments of any of the embodiments of the invention, the process comprises isomerizing at least a portion of the unsaturated macrocyclic compound in a first mixture to obtain a second mixture having a different isomeric purity than that of the first mixture, and contacting the ion exchange medium comprising silver ions with the second mixture.

According to some embodiments of any of the embodiments of the invention, an isomeric purity of the second mixture is closer to thermodynamic equilibrium between geometric isomers of the unsaturated macrocyclic compound than is an isomeric purity of the first mixture.

According to some embodiments of any of the embodiments of the invention, the isomerizing is effected by contact with an aluminum salt at a temperature of at least 80° C.

According to some embodiments of any of the embodiments of the invention, the isomerizing is effected by contact with aluminum nitrate.

According to some embodiments of any of the embodiments of the invention, the isomerizing is effected at a temperature of at least 100° C.

According to some embodiments of any of the embodiments of the invention, the unsaturated macrocyclic compound comprises a ring of at least 10 atoms.

According to some embodiments of any of the embodiments of the invention, the unsaturated macrocyclic compound comprises a ring of at least 12 atoms.

According to some embodiments of any of the embodiments of the invention, the unsaturated macrocyclic compound is an unsaturated ketone.

According to some embodiments of any of the embodiments of the invention, the unsaturated macrocyclic compound is selected from the group consisting of a cycloalkenone and an oxacycloalkenone.

According to some embodiments of any of the embodiments of the invention, the cycloalkenone and/or the oxacycloalkenone is unsubstituted or substituted by methyl.

According to some embodiments of any of the embodiments of the invention, the oxacycloalkenone is a lactone (1-oxacycloalken-2-one).

According to some embodiments of any of the embodiments of the invention, the oxacycloalkenone is a ketone.

According to some embodiments of any of the embodiments of the invention, the cyclic ketone is selected from the group consisting of a cyclotetradecenone (optionally 3-methyl-cyclotetradec-3-en-1-one, 3-methyl-cyclotetradec-5-en-1-one and/or 3-methyl-cyclotetradec-3,10-dien-1-one), a cyclopentadecenone (optionally cyclopentadec-4-en-1-one, 3-methyl-cyclopentadec-2-en-1-one, 3-methyl-cyclopentadec-3-en-1-one, 3-methyl-cyclopentadec-4-en-1-one and/or 3-methyl-cyclopentadec-5-en-1-one), a cyclohexadecenone (optionally cyclohexadec-8-en-1-one, cyclohexadec-5-en-1-one and/or 3-methyl-cyclohexadec-3-en-1-one), and a cycloheptadecenone (optionally cycloheptadec-9-en-1-one and/or 3-methyl-cycloheptadec-3-en-1-one), and the lactone is selected from the group consisting of an oxacyclotetradecen-2-one, an oxacyclopentadecen-2-one (optionally 13-methyl-oxacyclopentadec-10-en-2-one), an oxacyclohexadecen-2-one (optionally oxacyclohexadec-3-en-2-one, oxacyclohexadec-8-en-2-one, oxacyclohexadec-4,8-dien-2-one, oxacyclohexadec-12-en-2-one and/or oxacyclohexadec-13-en-2-one), and an oxacycloheptadecen-2-one (optionally oxacycloheptadec-8-en-2-one and/or oxacycloheptadec-10-en-2-one).

According to some embodiments of any of the embodiments of the invention, the unsaturated macrocyclic compound comprises a single carbon-carbon double bond, and the geometric isomers comprise the cis isomer and the trans isomer.

Herein and in the art, the term "double bond" refers to a bond between two atoms wherein the bond involves four bonding electrons, e.g., instead of two bonding electrons as is typical of saturated bonds. For example, a double bond between two carbon atoms (carbon-carbon double bond) refers to a bond between two carbon atoms wherein the bond involves four bonding electrons.

According to some embodiments of any of the embodiments of the invention of an odoriferous compound, an antibiotic compound, an antiviral compound, an anti-parasitic agent, an anti-proliferative agent, an immune-modulating compound, and an antifungal compound.

According to some embodiments of any of the embodiments of the invention, the unsaturated macrocyclic compound is an odoriferous compound.

According to some embodiments of any of the embodiments of the invention, the unsaturated macrocyclic compound is selected from the group consisting of archazolid B, BI 201302, BILN 2061, bryostatins, cryptophycins, cyclotrienins, dactylolide, 9,10-dehydroepothiolones, FD-891, FR-901375, longithorones, mycolactones, nakadomarin A, pacritinib, rhizopodin, rhizoxin, romidepsin, SB1317, spiruchostatins, tedanolide, thailandepsins, upenamide, WF-1360F, and zampanolide.

According to some embodiments of any of the embodiments of the invention, the unsaturated macrocyclic compound is a naturally occurring unsaturated macrocyclic compound, being obtained from a natural source or prepared synthetically.

According to some embodiments of any of the embodiments of the invention, the unsaturated macrocyclic compound is a plant-derived unsaturated macrocyclic compound, comprising a mixture of two geometric isomers of the macrocyclic compound, optionally in a concentration ratio in a range of from 10:1 to 40:1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
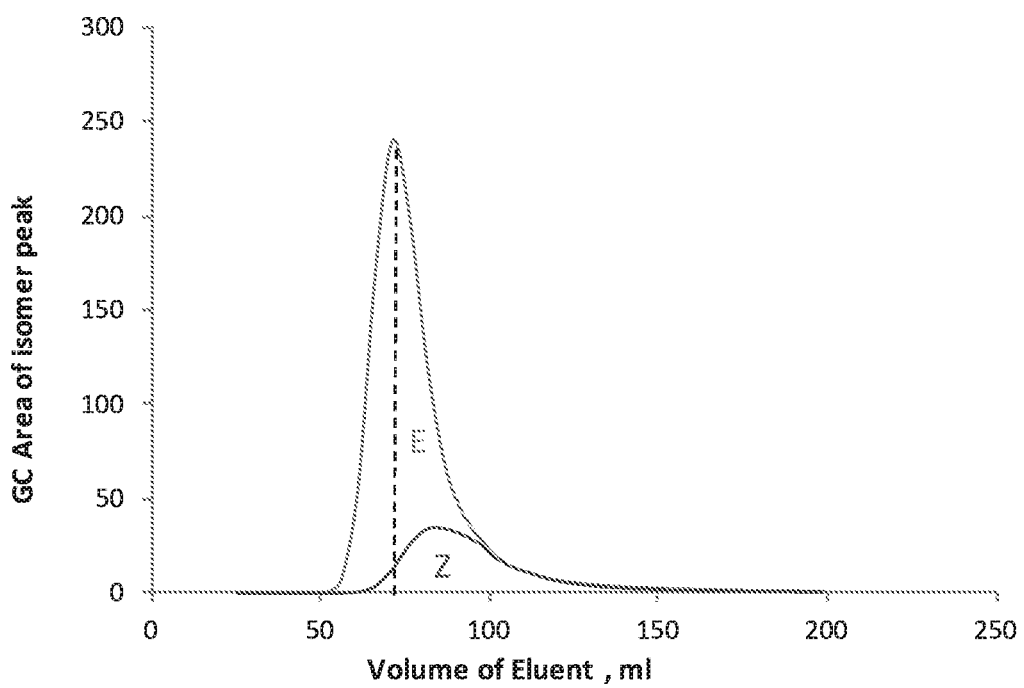
FIG. 1 is a graph showing amounts of E (high peak) and Z (low peak) isomers of oxacycloheptadec-10-en-2-one (as determined by gas chromatography (GC); arbitrary area units) eluted with methanol as solvent from a silver ion-loaded ion exchange column as a function of amount of solvent passed through the column (dashed line indicates maximum for E isomer).

The present invention, in some embodiments thereof, relates to purification, and more particularly, but not exclusively, to purification of macrocyclic compounds.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered that an ion exchange medium loaded with silver ions is surprisingly effective at purifying isomers of unsaturated macrocyclic compounds. While reducing the present invention to practice, the inventors separated commercially valuable macrocyclic "musk" compounds from geometric isomers thereof as well as from other, optionally structurally similar, macrocyclic molecules, and prepared samples of individual isomers of such compounds characterized by a high isomer purity.

The present invention allows purification, for example, of economically valuable macrocyclic compounds in a convenient and cost-effective manner.

The present invention allows providing highly pure isomers of macrocyclic compounds.

Furthermore, embodiments of the present invention render economical the synthetic preparations of purified isomers of unsaturated macrocyclic compounds which have heretofore been prepared solely from natural sources already characterized by high isomeric purity, thus allowing the provision of synthetically prepared purified isomers of unsaturated macrocyclic compounds.

According to an aspect of some embodiments of the invention, there is provided a process of obtaining a purified geometric isomer (as defined herein, according to any of the respective embodiments) of an unsaturated macrocyclic compound (as defined herein, according to any of the respective embodiments). The process comprises contacting an ion exchange medium comprising silver ions (according to any of the respective embodiments described herein) with a mixture comprising at least one geometric isomer of the unsaturated macrocyclic compound, to thereby obtain at least one fraction comprising a purified geometric isomer of the macrocyclic compound.

The mixture may optionally comprise two or more geometric isomers (in admixture) and/or at least one additional compound other than the aforementioned unsaturated macrocyclic compound (e.g., a compound that is structurally similar to the unsaturated macrocyclic compound, such as, but not limited to, an additional unsaturated macrocyclic compound, a saturated macrocyclic compound and/or a compound other than a macrocyclic compound, as further defined herein).

Macrocyclic Compound:

Herein, the term "macrocyclic compound" refers to a compound comprising a ring having at least 8 atoms therein, i.e., an 8-membered ring or larger ring.

Herein, the term "unsaturated macrocyclic compound" refers to a macrocyclic compound (as defined herein, according to any of the respective embodiments) which comprises at least one unsaturated carbon-carbon bond, preferably comprising at least one carbon-carbon double bond.

Herein and in the art, the term "geometric isomer" refers to isomers that have the same molecular formula and sequence of bonded atoms (constitution), but differ in the relative orientation of functional groups within the molecule, for example, wherein one geometric isomer could theoretically be converted to another geometric isomer by rotation of one or more bonds which do not freely rotate in practice (e.g., double bonds). The IUPAC-endorsed convention of designating E and Z geometric isomers with respect to individual double bonds is well known in the art.

In some embodiments of any of the embodiments described herein, the unsaturated macrocyclic compound comprises at least one unsaturated bond (preferably comprising at least one double bond, as defined herein) between two ring carbons.

In some embodiments of any of the embodiments described herein, the unsaturated macrocyclic compound comprises a ring of at least 9 atoms. In some such embodiments, the unsaturated macrocyclic compound comprises a ring of at least 10 atoms. In some such embodiments, the unsaturated macrocyclic compound comprises a ring of at least 11 atoms. In some such embodiments, the unsaturated macrocyclic compound comprises a ring of at least 12 atoms. In some such embodiments, the unsaturated macrocyclic compound comprises a ring of at least 13 atoms. In some such embodiments, the unsaturated macrocyclic compound comprises a ring of at least 14 atoms.

In some of any of the embodiments described herein, the unsaturated macrocyclic compound comprises a ring of 8 atoms, or a ring of 9 atoms, or a ring of 10 atoms, or a ring of 11 atoms, or a ring of 12 atoms, or a ring of 13 atoms, or a ring of 14 atoms, or a ring of 15 atoms, or a ring of 16 atoms, or higher rings, of, for example, 17, 18, 19, 20 and more atoms (e.g., up to 30 atoms).

In some of any of the embodiments described herein, the atoms in a ring (of at least 8 atoms) of a macrocyclic compound (according to any of the respective embodiments described herein) are each independently a carbon, nitrogen, oxygen or sulfur atom. In some embodiments, the atoms in the ring are each a carbon or oxygen atom. In some embodiments, the atoms in the ring are each a carbon atom (e.g., in a cycloalkenone).

In some of any of the embodiments described herein, the atoms in a ring (of at least 8 atoms) of a macrocyclic compound (according to any of the respective embodiments described herein) include mostly (e.g., at least 60%, or at least 70%, or at least 80%, or at least 90% or 100%) carbon atoms, and optionally one or more heteroatoms (e.g., oxygen, nitrogen and/or sulfur atoms).

In some embodiments of any of the embodiments described herein, the unsaturated macrocyclic compound comprises a single carbon-carbon double bond, and the geometric isomers in a mixture thereof comprise the cis isomer and the trans isomer of the unsaturated macrocyclic compound.

In some embodiments of any of the embodiments described herein, the unsaturated macrocyclic compound comprises two carbon-carbon double bonds, and the geometric isomers in a mixture thereof comprise at least two of the cis/cis isomer, cis\trans isomer, trans/trans isomer and the trans/cis isomer of the unsaturated macrocyclic compound.

In some embodiments of any of the embodiments described herein, the unsaturated macrocyclic compound is a ketone (comprising at least one unsaturated carbon-carbon bond), i.e., the compound comprises at least one carbon atom substituted by an oxo ($=O$) group, which is further attached to two adjacent carbon atoms. In some embodiments, the oxo-substituted carbon and the two adjacent carbon atoms are each ring carbon atoms (e.g., the backbone of the ring is substituted by the oxo group).

In some embodiments of any of the embodiments described herein, the unsaturated macrocyclic compound is a cycloalkenone or an oxacycloalkenone.

Herein, the term "cycloalkenone" refers to an alicyclic compound (e.g., an alicyclic unsaturated macrocyclic compound according to any of the respective embodiments described herein) having a ring of carbon atoms, comprising at least one double-bond between two ring carbon atoms, wherein at least one ring carbon atom is substituted by an oxo ($=O$) group. The cycloalkenone may be further substituted or non-substituted.

In some embodiments of any of the respective embodiments described herein, the cycloalkenone (e.g., a ketone according to any of the respective embodiments described herein) is a cyclotetradecenone (a cycloalkenone having a 14-membered ring), a cyclopentadecenone (a cycloalkenone having a 15-membered ring), a cyclohexadecenone (a cycloalkenone having a 16-membered ring) or a cycloheptadecenone (a cycloalkenone having a 17-membered ring).

Examples of suitable cyclotetradecenones include, without limitation, 3-methyl-cyclotetradec-3-en-1-one, 3-methyl-cyclotetradec-5-en-1-one and 3-methyl-cyclotetradec-3,10-dien-1-one). Purified (5E)-3-methyl-cyclotetradec-5-en-1-one is a non-limiting example of a purified geometric isomer of 3-methyl-cyclotetradec-5-en-1-one.

Examples of suitable cyclopentadecenones include, without limitation, cyclopentadec-4-en-1-one, 3-methyl-cyclopentadec-2-en-1-one, 3-methyl-cyclopentadec-3-en-1-one, 3-methyl-cyclopentadec-4-en-1-one and 3-methyl-cyclopentadec-5-en-1-one. (4E)-Cyclopentadec-4-en-1-one and (4Z)-cyclopentadec-4-en-1-one are exemplary geometric isomers purified according to some embodiments described herein, with purified (4Z)-cyclopentadec-4-en-1-one being an example of a particularly desirable purified isomer (e.g., which is marketed under the tradename Exaltenone™). (4E)-3-Methyl-cyclopentadec-4-en-1-one and (4Z)-3-methyl-cyclopentadec-4-en-1-one are exemplary geometric isomers purified according to some embodiments described herein, with purified (4E)-3-methyl-cyclopentadec-4-en-1-one being an example of a particularly desirable purified isomer. (5E)-3-Methyl-cyclopentadec-5-en-1-one (optionally (3R/S,5E)-3-methyl-cyclopentadec-5-en-1-one) and (5Z)-3-methyl-cyclopentadec-5-en-1-one are exemplary geometric isomers purified according to some embodiments described herein, with purified (5E)-3-methyl-cyclopentadec-5-en-1-one being an example of a particularly desirable purified isomer.

Examples of suitable cyclohexadecenones include, without limitation, cyclohexadec-8-en-1-one, cyclohexadec-5-en-1-one and 3-methyl-cyclohexadec-3-en-1-one. (8Z)-Cyclohexadec-8-en-1-one and (8E)-cyclohexadec-8-en-1-one are exemplary geometric isomers purified according to some embodiments herein, with purified (8E)-cyclohexadec-8-en-1-one being an example of a particularly desirable purified isomer (e.g., which is marketed under the tradename Globanone™) Purified (5Z)-cyclohexadec-5-en-1-one is a non-limiting example of a purified geometric isomer of cyclohexadec-5-en-1-one.

Examples of suitable cycloheptadecenones include, without limitation, cycloheptadec-9-en-1-one (also known as "civetone") and 3-methyl-cycloheptadec-3-en-1-one. (9Z)-Cycloheptadec-9-en-1-one is an exemplary geometric isomer purified according to some embodiments described herein.

Herein, the term "oxacycloalkenone" refers to a heteroalicyclic compound (e.g., a heteroalicyclic unsaturated macrocyclic compound according to any of the respective embodiments described herein) having a ring consisting of carbon atoms and at least one oxygen atom, comprising at least one double-bond between two ring carbon atoms, wherein at least one ring carbon atom is substituted by an oxo (=O) group (thereby forming a ketone). The oxacycloalkenone may be further substituted or non-substituted.

An oxacycloalkenone may optionally be a lactone (i.e., a 1-oxacycloalken-2-one), wherein a ring oxygen atom (e.g., designated as the 1-position) is adjacent to an oxo-substituted carbon atom (e.g., designated as the 2-position), thereby forming a —O—C(=O)— group in the ring.

Alternatively or additionally, an oxacycloalkenone may be an ether (e.g., wherein a ring oxygen atom is between two carbon atoms which are not oxo-substituted). An ether oxacycloalkenone may optionally be a ketone, wherein oxo-substituted carbon atom is attached to two carbon atoms, for example, in an oxacycloalkenone comprising only one ring oxygen and only one oxo-substituted ring carbon.

In some embodiments of any of the embodiments described herein, the unsaturated macrocyclic compound is unsubstituted (except optionally by one or more oxo groups) or substituted by an alkyl, e.g., methyl (and optionally further by one or more oxo groups). In some embodiments, the unsaturated macrocyclic compound is a cycloalkenone or oxacycloalkenone (as defined herein according to any of the respective embodiments) which is unsubstituted or substituted by an alkyl, e.g., methyl.

In some embodiments of any of the respective embodiments described herein, the oxacycloalkenone (e.g., a lactone according to any of the respective embodiments described herein) is an oxacyclotetradecen-2-one (an oxacycloalkenone lactone having a 14-membered ring), an oxacyclopentadecen-2-one (an oxacycloalkenone lactone having a 15-membered ring), an oxacyclohexadecen-2-one (an oxacycloalkenone lactone having a 16-membered ring) or an oxacycloheptadecen-2-one (an oxacycloalkenone lactone having a 17-membered ring). Examples of suitable oxacyclopentadecen-2-ones include, without limitation, 13-methyl-oxacyclopentadec-10-en-2-one (optionally (13R)-methyl-oxacyclopentadec-10-en-2-one or a (13R/S) racemate). Purified (10Z)-13-methyl-oxacyclopentadec-10-en-2-one (optionally (13R,10Z)-13-methyl-oxacyclopentadec-10-en-2-one or a (13R/S,10Z) racemate) is a non-limiting example of a purified geometric isomer of 13-methyl-oxacyclopentadec-10-en-2-one (e.g., which is marketed under the tradename Nirvanolide®).

Examples of suitable oxacyclohexadecen-2-ones include, without limitation, oxacyclohexadec-3-en-2-one, oxacyclohexadec-8-en-2-one, oxacyclohexadec-4,8-dien-2-one, oxacyclohexadec-12-en-2-one, and oxacyclohexadec-13-en-2-one. (12E)-oxacyclohexadec-12-en-2-one and (13E)-oxacyclohexadec-13-en-2-one are exemplary geometric isomers (of oxacyclohexadec-12-en-2-one and oxacyclohexadec-13-en-2-one, respectively) purified according to some embodiments herein.

Examples of suitable oxacycloheptadecen-2-ones include, without limitation, oxacycloheptadec-8-en-2-one (also known as "ambrettolide") and oxacycloheptadec-10-en-2-one (also known as "iso-ambrettolide", and which should not be confused with ambrettolide (oxacycloheptadec-8-en-2-one), although (10E)-iso-ambrettolide is marketed under the tradename Ambrettolide®)). (10Z)-oxacycloheptadec-10-en-2-one and (10E)-oxacycloheptadec-10-en-2-one are exemplary geometric isomers purified according to some embodiments herein, with purified (10E)-oxacycloheptadec-10-en-2-one being an example of a particularly desirable purified isomer. Purified (8Z)-oxacycloheptadec-8-en-2-one is a non-limiting example of a purified geometric isomer of oxacycloheptadec-8-en-2-one.

Without being bound by any particular theory, it is believed that many unsaturated macrocyclic compounds such as described hereinabove (e.g., cycloalkenones and oxacycloalkenones) are odoriferous compounds in general, and odoriferous compounds characterized by a "musk" odor in particular.

Nevertheless, unsaturated macrocyclic compounds having other uses and/or applications are also encompassed by the invention, in addition to odoriferous compounds. Thus, the unsaturated macrocyclic compound (according to any of the respective embodiments described herein) may optionally be, for example, an antibiotic compound (e.g., nakadomarin A), an antiviral compound (e.g., BI 201302, BILN 2061), an anti-parasitic agent, an anti-proliferative agent (e.g., bryostatins, cryptophycins, cyclotrienins, dactylolide, 9,10-dehydroepothiolones, FR-901375, longithorones, nakadomarin A, pacritinib, rhizopodin, rhizoxin, romidepsin, SB1317, spiruchostatins, tedanolide, thailandepsins, WF-1360F or zampanolide), an immune-modulating compound (e.g., archazolid B, FD-891, mycolactones), and/or an antifungal compound (e.g., nakadomarin A, rhizopodon).

Further examples of unsaturated macrocyclic compounds encompassed by embodiments of the invention include, without limitation, archazolid B, BI 201302, BILN 2061, bryostatins (e.g., bryostatin 1), cryptophycins (e.g., cryptophycin-52), cyclotrienins (e.g., cyclotrienin I, cyclotrienin II, cyclotrienin III or cyclotrienin IV), dactylolide, 9,10-dehydroepothiolones (e.g., 9,10-dehydroepothiolone C or 9,10-dehydroepothiolone D), FD-891, FR-901375, longithorones (e.g., longithorone A), mycolactones (e.g., mycolactone A, mycolactone B, mycolactone C, mycolactone D, mycolactone E or mycolactone F), nakadomarin A, pacritinib, rhizopodin, rhizoxin, romidepsin, SB1317, spiruchostatins (e.g., spiruchostatin A, spiruchostatin B), tedanolide, thailandepsins (e.g., thailandepsin A, thailandepsin B), upenamide, WF-1360F, and zampanolide.

In some embodiments of any of the respective embodiments described herein, the unsaturated macrocyclic compound is a naturally occurring unsaturated macrocyclic compound, which is present in a natural source. In some embodiments, the natural source is a plant. In some embodiments, the unsaturated macrocyclic compound is obtained from the natural source (e.g., is extracted from the natural source). In some embodiments, the unsaturated macrocyclic compound is prepared synthetically. In some embodiments, the macrocyclic compound is prepared synthetically from another compound (optionally a saturated or unsaturated macrocyclic compound) which is obtained from a natural source (e.g., a plant), for example, the unsaturated macrocyclic compound is a semi-synthetic compound.

In some embodiments, the unsaturated macrocyclic compound is obtained from a plant or prepared synthetically from another compound obtained from a plant. Such compounds are also referred to herein collectively as plant-derived unsaturated macrocyclic compounds. In some embodiments, the plant-derived compound has a relatively high purity of a geometric isomer, for example, wherein a concentration ratio of two geometric isomers therein is at least 10:1, optionally in a range of form 10:1 to 40:1. In some such embodiments, the process comprises purifying the less prevalent geometric isomer in the plant-derived compound, for example, by utilizing isomerization according to any of the respective embodiments described herein to convert the less prevalent isomer to a desired isomer.

Alternatively, in some embodiments, the process comprises purifying the more prevalent geometric isomer in the plant-derived compound, for example, by increasing the purity to even higher than that present in the plant-derived compound.

In some embodiments, the unsaturated macrocyclic compound is a plant-derived unsaturated macrocyclic compound, being obtained from a plant or prepared synthetically from another compound obtained from a plant. In some embodiments, the plant-derived compound has a relatively high purity of a geometric isomer, for example, wherein a concentration ratio of two geometric isomers therein is at least 10:1, optionally in a range of form 10:1 to 40:1.

Herein, a "purity" of an isomer indicated herein, also referred to herein interchangeably as an "isomeric purity", refers to a percentage of a total amount of a molecule (characterized by multiple possible geometric isomers) which is in a form of the indicated geometric isomer. Thus, for example, a purity of 90% refers to 90% of a molecule being in a form of an indicated geometric isomer, and 10% of the molecule being in a form of one or more other geometric isomers.

Chromatography:

In some embodiments of any of the embodiments described herein, the process comprises chromatography, for example, wherein the stationary phase comprises an ion exchange medium (according to any of the respective embodiments described herein) and/or a mobile phase comprises a solvent according to any of the respective embodiments described herein (e.g., wherein the solvent is the mobile phase). In some embodiments, the ion exchange medium (according to any of the respective embodiments described herein) is in a form of a chromatography column. In some embodiments, the solvent (according to any of the respective embodiments described herein) is used as an eluent.

It is to be appreciated that the phrase "ion exchange medium" is not in any way intended to imply that ion exchange chromatography is effected, and merely refers to a type of substance, as detailed herein.

Herein, the term "column" (in the context of chromatography) refers to an enclosed space comprising a medium (e.g., ion exchange medium with silver ions, according to any of the respective embodiments described herein) therein, and being configured for having a solvent flow through the column, for example, by entering via an inlet on one side column and exiting via an outlet on another side of the column. The column may have any suitable shape, and is not intended to be further limiting with respect to shape.

In some embodiments of any of the embodiments described herein, the process comprises batch chromatography. In some embodiments, the process comprises eluting fractions from a single chromatography column comprising the ion exchange medium with silver ions (according to any of the respective embodiments described herein).

In some embodiments of any of the embodiments described herein, the process comprises simulated moving bed (SMB) chromatography.

Herein and in the art, the phrase "simulated moving bed" refers to a process wherein locations of inlets (e.g., feed inlet and solvent inlet) and outlets (e.g., desired and undesired product outlets) are moved relative to a stationary phase; by moving the inlets and outlets and/or by moving the stationary phase (e.g., relative to fixed inlets and outlets). Such a process is similar to moving the stationary phase ("bed"), e.g., through a column with fixed inlets and outlets; whence the phrase "simulated moving bed". Systems for effecting SMB chromatography (and general instructions for their use) will be readily available to the skilled person.

The stationary phase may optionally be in a form of a loop, such that movement of the inlets/outlets relative to the stationary phase may continue indefinitely by going around the loop.

The stationary phase may optionally be in a form of a plurality (e.g., 10-25) interconnected chromatography columns (e.g., interconnected to form a loop), wherein movement of each inlet or outlet relative to the stationary phase comprises moving from one column to another column, for example, from the beginning of one column (as determined by direction of solvent flow within the column) to the beginning of another column. In some embodiments, an inlet and/or outlet moves from one column to an adjacent (directly connected) column, that is, in steps of one column at a time.

Movement of an inlet or outlet may optionally be effected by moving a port configured for operating as an inlet or outlet relative to fixed chromatography columns, or alternatively, by moving chromatography columns relative to a fixed port configured for operating as an inlet or outlet.

In some embodiments of any of the embodiments described herein relating to SMB chromatography, the process comprises providing a mixture (according to any of the respective embodiments described herein) via a first inlet (also referred to herein as a "feed" inlet or port), providing a solvent (according to any of the respective embodiments described herein) via a second inlet, and removing a fraction comprising a purified geometric isomer (according to any of the respective embodiments described herein) via a third inlet (also referred to herein as an "extract" inlet or port).

In some embodiments, the process further comprises removing a fraction comprising a lower purity of the geometric isomer purified according to any of the respective embodiments described herein (e.g., a second geometric isomer in purified form) via a fourth inlet (also referred to herein as a "raffinate" inlet or port) and/or removing solvent and/or impurities other than the unsaturated macrocyclic compound (optionally unspecified impurities) via a fifth inlet (also referred to herein as a "purge" inlet or port). In some embodiments, the fifth inlet may be immediately before the second inlet (e.g., one column before), for example, such that used solvent exits via the fifth (purge) inlet and the system is quickly thereafter replenished by fresh solvent via the second (solvent) inlet.

In the context of SMB, a "fraction" described herein may optionally refer to extract, purge or raffinate, and the like.

The length of an ion exchange medium with silver ions (e.g., total length of columns) in an SMB loop may optionally be in a range of from about 4 to about 15 meters, optionally from about 5 to about 10 meters.

Ion Exchange Medium:

Herein, the phrase "ion exchange medium" refers to a porous substance (e.g., a resin or polymer) capable of non-covalently and reversibly binding to ions (e.g., cations).

An ion exchange medium according to some embodiments of the invention is capable of binding to silver cations, for example, upon release of another cation (e.g., $Na^+$, $K^+$ and/or $H^+$) reversibly bound to the medium, to thereby form an ion exchange medium comprising silver ions according to any of the respective embodiments described herein.

In some embodiments of any of the embodiments described herein, the ion exchange medium is in a form of beads. In some embodiments, an average diameter of the beads is no more than 1 mm, optionally no more than 0.5 mm.

A porosity of an ion exchange medium in a form of beads may optionally be associated with spaces between the beads and/or porosity of individual beads.

In some embodiments of any of the embodiments described herein, the ion exchange medium comprises sulfonic acid groups (—$S(=O)_2OH$ groups) and/or a salt of sulfonic acid groups (e.g., —$S(=O)_2$—$O^-$ $X^+$, wherein $X^+$ is a cation, optionally $Ag^+$). In some such embodiments, the sulfonic acid groups are substituents of a polymer, for example, crosslinked polystyrene substituted by sulfonic acid groups (or a salt thereof).

In some embodiments of any of the embodiments described herein, the ion exchange medium comprises silver sulfonate groups (—$S(=O)_2$—$O^-$ $Ag^+$ groups).

In some embodiments of any of the embodiments described herein, the ion exchange medium comprises a polymer, optionally a crosslinked polymer. Crosslinked polystyrene sulfonate (e.g., crosslinked by divinylbenzene residues) is an exemplary polymer in an ion exchange medium.

Crosslinked polystyrene sulfonate ion exchange resin suitable for use in some embodiments of the invention is widely available from commercial sources, for example, as Purolite® PCR145K resin, Lewatit® SP 112 resin, or Dowex™ MSC-1 resin.

As exemplified herein, an ion exchange medium comprising silver ions may be prepared from a typical ion exchange medium (e.g., a commercially available crosslinked polystyrene sulfonate ion exchange resin) by removing water from the 1 ion exchange medium and contacting the medium with silver ions, for example, silver ions in a non-aqueous solvent (e.g., a non-aqueous polar solvent), to thereby effect ion exchange with silver ions.

In some embodiments of any of the embodiments described herein, at least 60% of the cations of the ion exchange medium are silver ions. In some embodiments, at least 70% of the cations of the ion exchange medium are silver ions. In some embodiments, at least 80% of the cations of the ion exchange medium are silver ions.

In some embodiments, at least 85% of the cations of the ion exchange medium are silver ions. In some embodiments, at least 90% of the cations of the ion exchange medium are silver ions. In some embodiments, at least 95% of the cations of the ion exchange medium are silver ions. In some embodiments, substantially all of the cations of the ion exchange medium are silver ions.

Herein, the phrase "cations of the ion exchange medium" refers to cations which are non-covalently bound to the ion exchange medium (e.g., via electrostatic attraction to negative charges in the ion exchange medium) and to reversibly bound cations (e.g., $H^+$) which can be replaced by the aforementioned cations which non-covalently bind to the medium (e.g., upon contact with a solution comprising such cations which non-covalently bind to the medium). The number of cations is indicated by the number of positive charges thereof, e.g., such that a divalent cation is considered as two cations. The number of cations may thus be regarded as a capacity of the ion exchange medium for univalent cations.

A percentage of cations of the ion exchange medium which are silver ions may optionally be calculated by determining an amount of silver ions in an indicated ion exchange medium and determining (e.g., separately) a capacity of the indicated medium for a reference (univalent) cation (optionally $Na^+$), for example, by contacting the indicated medium (or a corresponding sample of ion exchange medium) with the reference cation under conditions which allow for maximal binding of the reference cation (e.g., by eliminating binding of any other cation). Such a capacity of a medium for a reference cation (e.g., $Na^+$) may optionally be provided, for example, by a manufacturer's specification for the ion exchange medium. The percentage of cations of the ion exchange medium which are silver ions can thus be calculated by dividing the amount of silver ions in the ion exchange medium by the capacity of the same medium for the reference cation.

In some embodiments of any of the embodiments described herein, a concentration of silver ions in the ion exchange medium is at least 20% by weight of the total dry weight of the ion exchange medium (including the weight of silver ions in the medium). In some such embodiments, the concentration of silver ions in the ion exchange medium is at least 22% by weight of the total dry weight of the ion exchange medium. In some embodiments, the concentration of silver ions in the ion exchange medium is at least 24% by weight of the total dry weight of the ion exchange medium. In some embodiments, the concentration of silver ions in the ion exchange medium is at least 26% by weight of the total dry weight of the ion exchange medium. In some embodiments, the concentration of silver ions in the ion exchange medium is at least 28% by weight of the total dry weight of the ion exchange medium. In some embodiments, the concentration of silver ions in the ion exchange medium is at least 30% by weight of the total dry weight of the ion exchange medium. In some embodiments, the concentration of silver ions in the ion exchange medium is at least 32% by weight of the total dry weight of the ion exchange medium. In some embodiments, the concentration of silver ions in the ion exchange medium is at least 34% by weight of the total dry weight of the ion exchange medium. In some embodiments, the concentration of silver ions in the ion exchange medium is about 34.5% by weight of the total dry weight of the ion exchange medium.

In some embodiments of any of the embodiments described herein, a concentration of silver ions in the ion exchange medium is no more than about 40% by weight of the total dry weight of the ion exchange medium (including the weight of silver ions in the medium). In some such embodiments, the concentration of silver ions in the ion exchange medium is no more than about 34.5% by weight of the total dry weight of the ion exchange medium.

In some embodiments of any of the embodiments described herein relating to SMB chromatography, a concentration of silver ions in an ion exchange medium is at least 20%, at least 24%, at least 26%, at least 28%, at least 30%, at least 32%, and even at least 34% (e.g., up to about 40% or up to about 34.5%), by weight of the total dry weight of the ion exchange medium, according to any of the respective embodiments described herein. In some such embodiments, a length of the ion exchange medium with silver ions in an SMB loop is from about 1 to about 4 meters, optionally from about 1.5 to about 3 meters.

In some embodiments of any of the embodiments described herein, a concentration of silver ions in the ion exchange medium is at least 0.1 gram silver ions per $cm^3$ (100 grams/liter). In some such embodiments, the concentration of silver ions in the ion exchange medium is in a range of from 0.1 to 0.3 gram silver ions per $cm^3$.

In some embodiments, the concentration of silver ions in the ion exchange medium is in a range of from 0.1 to 0.2 gram/$cm^3$. In some embodiments, the concentration of silver ions in the ion exchange medium is in a range of from 0.1 to 0.18 gram/$cm^3$. In some embodiments, the concentration of silver ions in the ion exchange medium is about 0.16 gram/$cm^3$.

In some embodiments of any of the embodiments described herein, a concentration of silver ions in the ion exchange medium is at least 0.12 gram silver ions per $cm^3$ (120 grams/liter). In some such embodiments, the concentration of silver ions in the ion exchange medium is in a range of from 0.12 to 0.3 gram silver ions per $cm^3$. In some embodiments, the concentration of silver ions in the ion exchange medium is in a range of from 0.12 to 0.2 gram/$cm^3$. In some embodiments, the concentration of silver ions in the ion exchange medium is in a range of from 0.12 to 0.18 gram/$cm^3$.

In some embodiments of any of the embodiments described herein, a concentration of silver ions in the ion exchange medium is at least 0.14 gram silver ions per $cm^3$ (140 grams/liter). In some such embodiments, the concentration of silver ions in the ion exchange medium is in a range of from 0.14 to 0.3 gram silver ions per $cm^3$. In some embodiments, the concentration of silver ions in the ion exchange medium is in a range of from 0.14 to 0.2 gram/$cm^3$. In some embodiments, the concentration of silver ions in the ion exchange medium is in a range of from 0.14 to 0.18 gram/$cm^3$.

In some embodiments of any of the embodiments described herein, a concentration of silver ions in the ion exchange medium is at least 0.16 gram silver ions per $cm^3$ (160 grams/liter). In some such embodiments, the concentration of silver ions in the ion exchange medium is in a range of from 0.16 to 0.3 gram silver ions per $cm^3$. In some embodiments, the concentration of silver ions in the ion exchange medium is in a range of from 0.16 to 0.2 gram/$cm^3$. In some embodiments, the concentration of silver ions in the ion exchange medium is in a range of from 0.16 to 0.18 gram/$cm^3$.

In some embodiments of any of the embodiments described herein relating to SMB chromatography, a concentration of silver ions in an ion exchange medium is at least 0.1 gram/$cm^3$, at least 0.12 gram/$cm^3$, at least 0.14 gram/$cm^3$, and even at least 0.16 gram/$cm^3$, according to any of the respective embodiments described herein (e.g., up to 0.2 or 0.3 gram/$cm^3$). In some such embodiments, a length of the ion exchange medium with silver ions in an SMB loop is from about 1 to about 4 meters, optionally from about 1.5 to about 3 meters.

In some embodiments of any of the embodiments described herein, the ion exchange medium with silver ions comprises a polystyrene sulfonate resin (e.g., PCR-145K) comprising silver ions at a concentration of about 0.16 gram/$cm^3$ and/or about 34.5% by weight (of the total dry weight of the ion exchange medium). In some such embodiments, the process comprises SMB chromatography (according to any of the respective embodiments described herein), wherein a length of the ion exchange medium with silver ions in an SMB loop is from about 1 to about 4 meters (optionally from about 1.5 to about 3 meters), and the ion exchange medium with silver ions is separated into from 10 to 25 columns (e.g., with inlet/outlet ports between the columns), optionally columns of from 100 to 150 cm in length.

In some embodiments of any of the embodiments described herein, a different medium comprising silver ions may be used instead of or in addition to an ion exchange medium with silver ions (according to any of the respective embodiments described herein. Such a medium is preferably used in addition to the use an ion exchange medium, e.g., wherein a process (according to any of the respective embodiments described herein) comprises at least one step of contacting an ion exchange medium comprising silver ions with a mixture of geometric isomers (according to any of the respective embodiments described herein) and at least one step (prior to and/or subsequently to the aforementioned step) of contacting a different medium comprising silver ions with a mixture of geometric isomers; for example, wherein a first step results in a partially purified geometric isomer and a subsequent step results in a purified geometric isomer (according to any of the respective embodiments described herein).

A gel comprising silver ions is a non-limiting example of a suitable medium comprising silver ions (other than an ion exchange medium). The gel may be, for example, a silica gel loaded with silver ions.

In some embodiments of any of the embodiments described herein, there is provided a process of obtaining a purified geometric isomer of an unsaturated macrocyclic compound (e.g., according to any of the embodiments described herein), the process comprising contacting a silica gel comprising silver ions with a mixture comprising at least one geometric isomer of the unsaturated macrocyclic compound, to thereby obtain at least one fraction comprising a purified geometric isomer of the macrocyclic compound (e.g., according to any of the embodiments described herein).

In some embodiments, a concentration of silver ions in a gel medium (e.g., silica gel) is at least 1 weight percent, optionally at least 2 weight percents, and optionally at least 5 weight percents; for example, wherein a concentration of silver ions therein is up to 7.5 weight percents, 10 weight percents, 15 weight percents, 20 weight percents, 25 weight percents, or even 30 weight percents or more (e.g., up to about 50 weight percents).

Conditions (e.g., temperature, flow rate, SMB parameters) for such a medium may optionally be as described herein according to any of the respective embodiments (e.g., in any of the embodiments relating to ion exchange medium).

In some embodiments of any of the embodiments described herein relating to a gel medium (e.g., silica gel), the macrocyclic compound is a lactone (e.g., according to any of the embodiments described herein), for example, an oxacycloheptadecen-2-one (e.g., oxacycloheptadec-10-en-2-one).

In some embodiments of any of the embodiments described herein relating to a gel medium (e.g., silica gel), the unsaturated macrocyclic compound (e.g., a cycloalkenone or oxacycloalkenone, according to any of the respective embodiments described herein) comprises a ring of at least 12 atoms (as described herein in any of the respective embodiments regarding the structure of the unsaturated macrocyclic compound). In some such embodiments, the unsaturated macrocyclic compound comprises a ring of at least 13 atoms (as described herein in any of the respective embodiments regarding the structure of the unsaturated macrocyclic compound). In some such embodiments, the unsaturated macrocyclic compound comprises a ring of at least 14 atoms (as described herein in any of the respective embodiments regarding the structure of the unsaturated macrocyclic compound). In some such embodiments, the unsaturated macrocyclic compound comprises a ring of at least 15 atoms (as described herein in any of the respective embodiments regarding the structure of the unsaturated macrocyclic compound). In some such embodiments, the unsaturated macrocyclic compound comprises a ring of at least 16 atoms (as described herein in any of the respective embodiments regarding the structure of the unsaturated macrocyclic compound). In some such embodiments, the unsaturated macrocyclic compound comprises a ring of at least 17 atoms (as described herein in any of the respective embodiments regarding the structure of the unsaturated macrocyclic compound).

Solvent:

In some embodiments of any of the embodiments described herein, the process further comprises contacting the ion exchange medium (according to any of the respective embodiments described herein) comprising silver ions with a solvent. The solvent may optionally be a single compound or a mixture of compounds (e.g., a solution). In some such embodiments, the solvent is an alcoholic and/or aqueous solvent.

In some embodiments of any of the embodiments described herein, the process further comprises chromatography (according to any of the respective embodiments described herein), wherein the solvent is a mobile phase and the ion exchange medium (according to any of the respective embodiments described herein) is comprised by a stationary phase.

Herein, the phrase "alcoholic and/or aqueous solvent" refers to a solvent wherein more than 50 weight percents of the solvent consists of one or more alcohols (e.g., methanol and/or ethanol), water, or a mixture thereof.

In some embodiments of any of the embodiments described herein relating to an alcoholic and/or aqueous solvent, at least 70 weight percents of the solvent consists of one or more alcohols (e.g., methanol and/or ethanol), water, or a mixture thereof. In some such embodiments, at least 90 weight percents of the solvent consists of one or more alcohols (e.g., methanol and/or ethanol), water, or a mixture thereof. In some embodiments, the solvent consists essentially of one or more alcohols (e.g., methanol and/or ethanol), water, or a mixture thereof.

In some embodiments of any of the embodiments described herein, a concentration of water in the solvent (e.g., an alcoholic and/or aqueous solvent, according to any of the respective embodiments described herein wherein the solvent comprises alcohol) is in a range of from 0 to 40 weight percents, the balance optionally consisting of one or more alcohols (e.g., methanol and/or ethanol). In some such embodiments, a concentration of water in the solvent is in a range of from 20 to 40 weight percents, the balance optionally consisting of one or more alcohols (e.g., methanol and/or ethanol). In exemplary embodiments, a concentration of water in the solvent is about 30 weight percents.

As exemplified herein, a solvent comprising water in combination with an alcohol (e.g., methanol) may allow for more effective purification than a solvent comprising the alcohol without water.

In some embodiments of any of the embodiments described herein, the solvent and/or ion exchange medium are selected such that the ion exchange medium does not dissolve in the solvent.

In some embodiments of any of the embodiments described herein, the solvent is contacted with an ion exchange medium comprising silver ions (according to any of the respective embodiments described herein) such that it flows through the ion exchange medium at a rate in a range of from 1 to 10 bed volumes per hour. In some embodiments, the rate is in a range of from 1 to 3 bed volumes per hour. In some embodiments, the rate is in a range of from 2 to 4 bed volumes per hour. In some embodiments, the rate is in a range of from 3 to 6 bed volumes per hour. In some embodiments, the rate is in a range of from 5 to 10 bed volumes per hour.

Herein and in the art, the term "bed volume" refers to a volume occupied by a medium, the medium herein being the ion exchange medium contacted with the solvent (according to any of the respective embodiments described herein).

In some embodiments of any of the embodiments described herein relating to a solvent flow rate in a range of from 1 to 10 bed volumes per hour (e.g., from 1 to 3, 2 to 4, 3 to 6 or 5 to 10 bed volumes per hour), a concentration of silver ions in an ion exchange medium is at least 20%, at least 24%, at least 26%, at least 28%, at least 30%, at least 32%, and even at least 34% (e.g., up to about 40% or up to about 34.5%), by weight of the total dry weight of the ion exchange medium, according to any of the respective embodiments described herein. Alternatively or additionally, in some such embodiments, a concentration of silver ions in an ion exchange medium is at least 0.1 gram/cm$^3$, at least 0.12 gram/cm$^3$, at least 0.14 gram/cm$^3$, and even at least 0.16 gram/cm$^3$, according to any of the respective embodiments described herein (e.g., up to 0.2 or 0.3 gram/cm$^3$).

In some embodiments of any of the embodiments described herein, the solvent is contacted with an ion exchange medium comprising silver ions (according to any of the respective embodiments described herein) such that it flows through the ion exchange medium at a rate in a range of from 2.5 to 250 cm per minute (corresponding to 2.5 to 250 ml solvent per cm$^2$ cross-section of the medium per minute). In some such embodiments, the solvent flows through the ion exchange medium (according to any of the respective embodiments described herein) at a rate in a range of from 2.5 to 8 cm per minute. In some such embodiments, the solvent flows through the ion exchange medium (according to any of the respective embodiments described herein) at a rate in a range of from 8 to 250 cm per minute. In some such embodiments, the solvent flows through the ion exchange medium (according to any of the respective embodiments described herein) at a rate in a range of from 12 to 120 cm per minute. In some such embodiments, the solvent flows through the ion exchange medium (according to any of the respective embodiments described herein) at a rate in a range of from 24 to 80 cm per minute.

In some embodiments of any of the embodiments described herein relating to a solvent flow rate in a range of from 2.5 to 250 cm per minute (e.g., from 2.5 to 8 cm per minute, from 8 to 250 cm, from 12 to 120 and/or from 24 to 80 cm per minute), a concentration of silver ions in an ion exchange medium is at least 20%, at least 24%, at least 26%, at least 28%, at least 30%, at least 32%, and even at least 34% (e.g., up to about 40% or up to about 34.5%), by weight of the total dry weight of the ion exchange medium, according to any of the respective embodiments described herein. Alternatively or additionally, in some such embodiments, a concentration of silver ions in an ion exchange medium is at least 0.1 gram/cm$^3$, at least 0.12 gram/cm$^3$, at least 0.14 gram/cm$^3$, and even at least 0.16 gram/cm$^3$, according to any of the respective embodiments described herein (e.g., up to 0.2 or 0.3 gram/cm$^3$).

A rate at which a solvent flows through an ion exchange medium may optionally be controlled, for example, by controlling a rate at which the solvent is contacted with the medium, by controlling a pressure differential (e.g., between a location at which the solvent initially contacts the medium and a location at which the solvent exits the medium) and/or by selecting a suitable porosity of ion exchange medium.

In some embodiments of any of the embodiments described herein, the solvent is contacted with an ion exchange medium comprising silver ions (according to any of the respective embodiments described herein) such that it flows through the ion exchange medium at a rate in a range of from about 2.5 to about 8 cm per minute. In some such embodiments, a concentration of silver ions in an ion exchange medium is at least 20%, at least 24%, at least 26%, at least 28%, at least 30%, at least 32%, and even at least 34% (e.g., up to about 40% or up to about 34.5%), by weight of the total dry weight of the ion exchange medium, according to any of the respective embodiments described herein. Alternatively or additionally, in some such embodiments, a concentration of silver ions in an ion exchange medium is at least 0.1 gram/cm$^3$, at least 0.12 gram/cm$^3$, at least 0.14 gram/cm$^3$, and even at least 0.16 gram/cm$^3$, according to any of the respective embodiments described herein (e.g., up to 0.2 or 0.3 gram/cm$^3$).

In some embodiments of any of the embodiments described herein, the solvent is contacted with an ion exchange medium comprising silver ions (according to any of the respective embodiments described herein) such that it flows through the ion exchange medium at a rate in a range of from about 8 to about 24 cm per minute. In some such embodiments, a concentration of silver ions in an ion exchange medium is at least 20%, at least 24%, at least 26%, at least 28%, at least 30%, at least 32%, and even at least 34% (e.g., up to about 40% or up to about 34.5%), by weight of the total dry weight of the ion exchange medium, according to any of the respective embodiments described herein. Alternatively or additionally, in some such embodiments, a concentration of silver ions in an ion exchange medium is at least 0.1 gram/cm$^3$, at least 0.12 gram/cm$^3$, at least 0.14 gram/cm$^3$, and even at least 0.16 gram/cm$^3$, according to any of the respective embodiments described herein (e.g., up to 0.2 or 0.3 gram/cm$^3$).

In some embodiments of any of the embodiments described herein, the solvent is contacted with an ion exchange medium comprising silver ions (according to any of the respective embodiments described herein) such that it flows through the ion exchange medium at a rate in a range of from about 24 to about 80 cm per minute. In some such embodiments, a concentration of silver ions in an ion exchange medium is at least 20%, at least 24%, at least 26%, at least 28%, at least 30%, at least 32%, and even at least 34% (e.g., up to about 40% or up to about 34.5%), by weight of the total dry weight of the ion exchange medium, according to any of the respective embodiments described herein. Alternatively or additionally, in some such embodiments, a concentration of silver ions in an ion exchange medium is at least 0.1 gram/cm$^3$, at least 0.12 gram/cm$^3$, at least 0.14 gram/cm$^3$, and even at least 0.16 gram/cm$^3$, according to any of the respective embodiments described herein (e.g., up to 0.2 or 0.3 gram/cm$^3$).

In some embodiments of any of the embodiments described herein, the solvent is contacted with an ion exchange medium comprising silver ions (according to any of the respective embodiments described herein) such that it flows through the ion exchange medium at a rate in a range of from about 80 to about 250 cm per minute. In some such embodiments, a concentration of silver ions in an ion exchange medium is at least 20%, at least 24%, at least 26%, at least 28%, at least 30%, at least 32%, and even at least 34% (e.g., up to about 40% or up to about 34.5%), by weight of the total dry weight of the ion exchange medium, according to any of the respective embodiments described herein. Alternatively or additionally, in some such embodiments, a concentration of silver ions in an ion exchange medium is at least 0.1 gram/cm$^3$, at least 0.12 gram/cm$^3$, at least 0.14 gram/cm$^3$, and even at least 0.16 gram/cm$^3$, according to any of the respective embodiments described herein (e.g., up to 0.2 or 0.3 gram/cm$^3$).

Process Steps:

In some embodiments of any of the embodiments described herein, contacting the ion exchange medium comprising silver ions with the mixture is effected such that a plurality of fractions is obtained.

In some such embodiments, at least one fraction (also referred to herein as a "first fraction") comprises a purified geometric isomer (according to any of the respective embodiments described herein), and at least one fraction (also referred to herein as a "second fraction") comprises the aforementioned geometric isomer at a purity which is lower than a purity of the geometric isomer in the first fraction.

The purity of the aforementioned geometric isomer in the second fraction(s) may optionally be greater than and/or lower than the purity of the geometric isomer in the mixture contacted with the ion exchange medium.

For example, the second fraction(s) may optionally be separated from the first fraction(s) because an isomeric purity in the second fraction(s), while enhanced relative to an isomeric purity of the mixture, is lower than a desired purity in a purified geometric isomer (e.g., according to any of the respective embodiments described herein).

Alternatively or additionally, the second fraction(s) may optionally comprise a greater purity (relative to the mixture) of a geometric isomer other than the isomer purified in the first fraction, such that separating the second fraction(s)

from the first fraction(s) effects separation of one geometric isomer (in the first fraction in purified form) from another geometric isomer (enriched in the second fraction(s)).

In some embodiments of any of the embodiments described herein, at least one second fraction (as defined herein) comprises a purified geometric isomer other than the geometric isomer purified in the first fraction (as defined herein), for example, when the mixture comprises only two geometric isomers of an unsaturated macrocyclic compound. In some such embodiments, the first fraction has a greater purity than the mixture with respect to one of the geometric isomers, and the second fraction has a lower purity than the mixture with respect to the aforementioned geometric isomer, and a greater purity than the mixture with respect to another geometric isomer.

In some embodiments of any of the embodiments described herein, the process further comprises contacting an ion exchange medium comprising silver ions (according to any of the respective embodiments described herein) with a second fraction, to thereby obtain at least one third fraction comprising a purified geometric isomer of the macrocyclic compound. In such embodiments, the second fraction may optionally be used as a mixture comprising at least one geometric isomer of the unsaturated macrocyclic compound (e.g., in an additional cycle of the process), the third fraction corresponding to a first fraction (although a purity and/or yield of the third fraction may be lower or higher than that of the first fraction).

In such a manner, any number of cycles of the process may be effected.

Herein, a "cycle" of a process refers to a part of the process in which a mixture of geometric isomers of an unsaturated macrocyclic compound (according to any of the respective embodiments described herein) is contacted with an ion exchange medium comprising silver ions and obtaining at least one fraction (according to any of the respective embodiments described herein), for example, in embodiments wherein the process comprises effecting a plurality of cycles, as defined herein. In each cycle, at least one fraction is obtained (as a result of the cycle) having a higher purity of a geometric isomer than a purity of the geometric isomer in the mixture contacted with the ion exchange medium in the respective cycle. Thus, the fraction obtained in one cycle may optionally be contacted in a further cycle with an ion exchange medium, to thereby obtain at least one fraction with an even higher purity of the geometric isomer.

Optionally, a purified geometric isomer (according to any of the respective embodiments described herein) is obtained during one or more cycles (e.g., comprising one or more fractions of a cycle), and the purified geometric isomer of different cycles may optionally be combined.

In some embodiments of any of the respective embodiments described herein, a cycle comprises passing a mixture of geometric isomers through an entire ion exchange medium comprising silver ions (e.g., according to any of the respective embodiments described herein), for example, through an entire chromatography stationary phase comprising the ion exchange medium (e.g., according to any of the respective embodiments described herein).

In some embodiments of any of the embodiments described herein relating to a process comprising a plurality of cycles, a mixture of isomers used in a cycle optionally comprises one or more fractions obtained in a previous cycle comprising a geometric isomer to be purified at a purity which is lower than a purity of the geometric isomer in the mixture used in the aforementioned previous cycle.

In embodiments wherein at least one second fraction is used in an additional cycle of the process (e.g., to thereby obtain at least one third fraction), the isomeric purity of the second fraction(s) may optionally greater than and/or lower than the purity of the geometric isomer in the mixture contacted with the ion exchange medium to obtain the second fraction(s). For example, in some such embodiments, the isomeric purity of the second fraction(s) is greater than that of the mixture contacted with the ion exchange medium to obtain the second fraction(s). Use of the second fraction (s) as a mixture in an additional cycle may optionally be advantageous for preparing a purified geometric isomer because the geometric isomer in the second fraction(s) is already partially purified.

In some embodiments of any of the embodiments described herein, the process further comprises increasing an isomeric purity of the geometric isomer in at least one second fraction, to thereby obtain at least one second fraction having an increased isomeric purity. The second fraction(s) having an increased isomeric purity may optionally be contacted with an ion exchange medium comprising silver ions, to thereby obtain at least one third fraction (e.g., in one or more additional cycle as described hereinabove).

For example, in some such embodiments, the isomeric purity of the second fraction(s) is depleted in a geometric isomer (e.g., a purity of the isomer is lower than that of the mixture contacted with the ion exchange medium to obtain the second fraction(s)), and increasing an isomeric purity of the geometric isomer in the second fraction(s) replenishes the second fraction with the geometric isomer, e.g., prior to an additional cycle.

Increasing an isomeric purity of the geometric isomer (e.g., a depleted geometric isomer) in at least one second fraction may optionally be effected prior to some or all of the cycles of a process comprising a plurality of cycles according to any of the respective embodiments described herein).

In some embodiments, increasing an isomeric purity of a second fraction(s) comprises combining the second fraction (s) with a mixture which has a greater purity (of the isomer to be purified) than the second fraction(s), for example, a mixture substantially identical to the mixture used to obtain the second fraction(s). Such combination may be effected, for example, so as to recycle depleted fractions which still have some of a desired geometric isomer and/or so as to recycle fractions in which the desired isomer is partially purified.

In some embodiments of any of the respective embodiments described herein, the process further comprises isomerizing at least a portion of an unsaturated macrocyclic compound in a first mixture comprising one or more geometric isomers to obtain a second mixture having a different isomeric purity (i.e., a different ratio of geometric isomers) than that of the first mixture. For example, an isomeric purity (e.g., expressed as a ratio of geometric isomers) of the second mixture may optionally be closer to a thermodynamic equilibrium between geometric isomers of an unsaturated macrocyclic compound than is the isomeric purity of the first mixture (e.g., when the ratio of geometric isomers in the first mixture is far from equilibrium).

Herein, the terms "isomerizing", "isomerization" and grammatical variations thereof refer to conversion of at least a portion of a geometric isomer of a molecule to one or more other geometric isomers of the molecule, for example, by effecting rotation around a double bond (e.g., conversion an E isomer to a Z isomer or vice versa). The "conversion" refers to net conversion, i.e., a difference between an initial state and a final state.

In some embodiments, increasing an isomeric purity of a second fraction(s) (according to any of the respective embodiments described herein) comprises isomerization, that is, conversion of one geometric isomer to another geometric isomer (the isomer whose purity is being increased). In some such embodiments, substantially all (i.e., at least 90%, and optionally at least 99%) of the unsaturated macrocyclic compound is eventually converted to a purified geometric isomer, for example, by performing a suitable number of cycles of contacting with an ion exchange medium (according to any of the respective embodiments described herein).

In some embodiments, the process further comprises contacting an ion exchange medium comprising silver ions (according to any of the respective embodiments described herein) with the second mixture. A cycle of isomerizing a first mixture to obtain a second mixture and contacting an ion exchange medium comprising silver ions with the second mixture may be effected once, or as multiple cycles (e.g., wherein a fraction obtained from one cycle is subjected to isomerization and contact an ion exchange medium in a subsequent cycle). In some such embodiments, contacting an ion exchange medium comprising silver ions with a second fraction having an increased isomeric purity (according to any of the respective embodiments described herein) is effected by using isomerization to effect at least a portion of the increase in isomeric purity (e.g., wherein the second mixture as described herein is a second fraction having an increased isomeric purity as described herein).

In some embodiments of any of the respective embodiments described herein, isomerizing an unsaturated macrocyclic compound is effected by contact with an aluminum salt at a temperature of at least 80° C. (e.g., up to 200° C. or up to about 300° C.). In some such embodiments, the temperature is at least 90° C. In some such embodiments, the temperature is at least 100° C. In some such embodiments, the temperature is at least 110° C. In some such embodiments, the temperature is at least 120° C. In some such embodiments, the temperature is at least 130° C. In some such embodiments, the temperature is at least 140° C. (e.g., from 140 to 200° C.). In some embodiments, the temperature is about 140° C.

Aluminum nitrate (e.g., $Al(NO_3)_3 \cdot 9H_2O$) is a non-limiting example of an aluminum salt suitable for effecting isomerization according to any of the respective embodiments described herein.

In some embodiments of any of the embodiments described herein (e.g., embodiments relating to SMB), contacting the ion exchange medium with the mixture is effected at a temperature in a range of from about 30° C. to about 60° C. In some embodiments, the temperature is in a range of from about 35° C. to about 60° C. In some embodiments, the temperature is in a range of from about 40° C. to about 60° C.

In some embodiments of any of the embodiments described herein relating to contacting the ion exchange medium with the mixture at a temperature in a range of from about 30° C. to about 60° C., the temperature remains in the indicated range for the duration of the contacting procedure (e.g., at least until the purified geometric isomer is obtained). In some such embodiments, the temperature is constant (i.e., within a range of ±5° C., optionally ±2° C., and optionally even ±1° C.) for the duration of the contacting procedure.

Without being bound by any particular theory, it is believed that the temperature ranges described herein allow for a suitable degree of affinity between the silver ions and the unsaturated macrocyclic compound which is sufficiently high to affect the rate at which the macrocyclic compound passes through the ion exchange medium, yet not so high as to prevent the macrocyclic compound from passing effectively through the ion exchange medium.

In some embodiments of any of the embodiments described herein (e.g., embodiments relating to batch chromatography), contacting the ion exchange medium with the mixture is effected at a first temperature, and the process further comprises eluting at least one fraction from the ion exchange medium at a second temperature.

In some embodiments relating to a second temperature, the second temperature is higher than the first temperature. In some such embodiments, the second temperature is at least about 20° C., and optionally in a range of from about 20° C. to about 80° C., and optionally in a range of from about 20° C. to about 60° C. In some embodiments, the second temperature is at least about 30° C., optionally in a range of from about 30° C. to about 80° C., and optionally in a range of from about 30° C. to about 60° C. In some embodiments, the second temperature is at least about 35° C., optionally in a range of from about 35° C. to about 80° C., and optionally in a range of from about 35° C. to about 60° C. In some such embodiments, the second temperature is at least about 40° C., optionally in a range of from about 40° C. to about 80° C., and optionally in a range of from about 40° C. to about 60° C.

In some embodiments relating to a first temperature, the first temperature is no more than about 30° C., optionally in a range of from about 0° C. to about 30° C. In some embodiments, the first temperature is no more than about 20° C., optionally in a range of from about −10° C. to about 20° C., and optionally in a range of from about 0° C. to about 20° C. In some such embodiments, the second temperature is no more than about 10° C., optionally in a range of from about −20° C. to about 10° C., optionally in a range of from about −10° C. to about 10° C., and optionally in a range of from about 0° C. to about 10° C.

Purified Geometric Isomer:

Herein, the phrase "purified geometric isomer" encompasses a particular geometric isomer per se (100% pure) as well as a particular geometric isomer as part of a composition comprising the geometric isomer at an isomeric purity (as defined herein) which is greater than an isomeric purity of the mixture comprising at least one geometric isomer (according to any of the respective embodiments described herein), and which isomeric purity (of the purified geometric isomer) is at least 80%. It is to be understood that a "purified geometric isomer" may comprise (unless indicated otherwise) any concentration of the respective geometric isomer of an unsaturated macrocyclic compound, and optionally any amount of compounds other than geometric isomers of the unsaturated macrocyclic compound (e.g., impurities), provided that the isomeric purity of the unsaturated macrocyclic compound is as defined hereinabove.

In some embodiments of any of the embodiments described herein, the obtained purified geometric isomer is characterized by recovery of the isomer being at least 20%. In some embodiments, the recovery of the geometric isomer is at least 30%. In some embodiments, the recovery of the geometric isomer is at least 40%. In some embodiments, the recovery of the geometric isomer is at least 50%. In some embodiments, the recovery of the geometric isomer is at least 60%. In some embodiments, the recovery of the geometric isomer is at least 70%. In some embodiments, the recovery of the geometric isomer is at least 80%. In some embodiments, the recovery of the geometric isomer is at least 90%.

Herein, the term "recovery" refers to a percentage of an indicated isomer in a mixture (according to any of the respective embodiments described herein) which is present in a purified geometric isomer obtained according to any of the respective embodiments described herein.

In some embodiments of any of the embodiments described herein, the purified geometric isomer is characterized by a purity of at least 90%. In some such embodiments, recovery of the isomer in the purified geometric isomer is at least 20%.

In some embodiments, the recovery of the geometric isomer is at least 30%.

In some embodiments, the recovery of the geometric isomer is at least 40%.

In some embodiments, the recovery of the geometric isomer is at least 50%.

In some embodiments, the recovery of the geometric isomer is at least 60%.

In some embodiments, the recovery of the geometric isomer is at least 70%.

In some embodiments, the recovery of the geometric isomer is at least 80%.

In some embodiments, the recovery of the geometric isomer is at least 90%.

In some such embodiments of any of the embodiments described herein, the purified geometric isomer is characterized by a purity of at least 95%. In some such embodiments, recovery of the isomer in the purified geometric isomer is at least 20%.

In some embodiments, the recovery of the geometric isomer is at least 30%.

In some embodiments, the recovery of the geometric isomer is at least 40%.

In some embodiments, the recovery of the geometric isomer is at least 50%.

In some embodiments, the recovery of the geometric isomer is at least 60%.

In some embodiments, the recovery of the geometric isomer is at least 70%.

In some embodiments, the recovery of the geometric isomer is at least 80%.

In some embodiments, the recovery of the geometric isomer is at least 90%.

In some embodiments of any of the embodiments described herein, the purified geometric isomer is characterized by a purity of at least 98%. In some such embodiments, recovery of the isomer in the purified geometric isomer is at least 20%.

In some embodiments, the recovery of the geometric isomer is at least 30%.

In some embodiments, the recovery of the geometric isomer is at least 40%.

In some embodiments, the recovery of the geometric isomer is at least 50%.

In some embodiments, the recovery of the geometric isomer is at least 60%.

In some embodiments, the recovery of the geometric isomer is at least 70%.

In some embodiments, the recovery of the geometric isomer is at least 80%.

In some embodiments, the recovery of the geometric isomer is at least 90%.

In some embodiments of any of the embodiments described herein, the purified geometric isomer is characterized by a purity of at least 99%. In some such embodiments, recovery of the isomer in the purified geometric isomer is at least 20%.

In some embodiments, the recovery of the geometric isomer is at least 30%.

In some embodiments, the recovery of the geometric isomer is at least 40%.

In some embodiments, the recovery of the geometric isomer is at least 50%.

In some embodiments, the recovery of the geometric isomer is at least 60%.

In some embodiments, the recovery of the geometric isomer is at least 70%.

In some embodiments, the recovery of the geometric isomer is at least 80%.

In some embodiments, the recovery of the geometric isomer is at least 90%.

In some embodiments of any of the embodiments described herein, the purified geometric isomer is characterized by a purity of at least 99.5%. In some such embodiments, recovery of the isomer in the purified geometric isomer is at least 20%.

In some embodiments, the recovery of the geometric isomer is at least 30%.

In some embodiments, the recovery of the geometric isomer is at least 40%.

In some embodiments, the recovery of the geometric isomer is at least 50%.

In some embodiments, the recovery of the geometric isomer is at least 60%.

In some embodiments, the recovery of the geometric isomer is at least 70%.

In some embodiments, the recovery of the geometric isomer is at least 80%.

In some embodiments, the recovery of the geometric isomer is at least 90%.

In some embodiments of any of the embodiments described herein, the purified geometric isomer is characterized by a purity of at least 99.8%. In some such embodiments, recovery of the isomer in the purified geometric isomer is at least 20%.

In some embodiments, the recovery of the geometric isomer is at least 30%.

In some embodiments, the recovery of the geometric isomer is at least 40%.

In some embodiments, the recovery of the geometric isomer is at least 50%.

In some embodiments, the recovery of the geometric isomer is at least 60%.

In some embodiments, the recovery of the geometric isomer is at least 70%.

In some embodiments, the recovery of the geometric isomer is at least 80%.

In some embodiments, the recovery of the geometric isomer is at least 90%.

In some embodiments of any of the embodiments described herein, the purified geometric isomer is characterized by a purity of at least 99.9%. In some such embodiments, recovery of the isomer in the purified geometric isomer is at least 20%.

In some embodiments, the recovery of the geometric isomer is at least 30%.

In some embodiments, the recovery of the geometric isomer is at least 40%.

In some embodiments, the recovery of the geometric isomer is at least 50%.

In some embodiments, the recovery of the geometric isomer is at least 60%.

In some embodiments, the recovery of the geometric isomer is at least 70%.

In some embodiments, the recovery of the geometric isomer is at least 80%.

In some embodiments, the recovery of the geometric isomer is at least 90%.

In some embodiments of any of the embodiments described herein, a mixture comprises a first geometric isomer and a second geometric isomer of an unsaturated macrocyclic compound (e.g., an unsaturated macrocyclic compound having only two geometric isomers), and the purified geometric isomer is a purified first geometric isomer. In some such embodiments, the process comprises separating the first geometric isomer and the second geometric isomer. For example, purification of a geometric isomer (according to any of the respective embodiments described herein) may refer essentially to separating the first geometric isomer and the second geometric isomer.

In some embodiments of any of the embodiments described herein, a purified first geometric isomer (according to any of the respective embodiments described herein) is characterized by a concentration ratio of first geometric isomer to second geometric isomer which is at least 150% of a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%. For example, a concentration ratio of 3:1 in a purified isomer would be 150% of a concentration ratio of 2:1 in the mixture, and a concentration ratio of 15:1 in a purified isomer would be 150% of a concentration ratio of 10:1 in the mixture.

In some embodiments of any of the embodiments described herein, a purified first geometric isomer (according to any of the respective embodiments described herein) is characterized by a concentration ratio of first geometric isomer to second geometric isomer which is at least 200% of (i.e., twice) a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%.

In some embodiments of any of the embodiments described herein, a purified first geometric isomer (according to any of the respective embodiments described herein) is characterized by a concentration ratio of first geometric isomer to second geometric isomer which is at least 300% of (i.e., 3-fold) a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%.

In some embodiments of any of the embodiments described herein, a purified first geometric isomer (according to any of the respective embodiments described herein) is characterized by a concentration ratio of first geometric isomer to second geometric isomer which is at least 500% of (i.e., 5-fold) a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%.

In some embodiments of any of the embodiments described herein, a purified first geometric isomer (according to any of the respective embodiments described herein) is characterized by a concentration ratio of first geometric isomer to second geometric isomer which is at least 1000% of (i.e., 10-fold) a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%.

In some embodiments of any of the embodiments described herein, a purified first geometric isomer (according to any of the respective embodiments described herein) is characterized by a concentration ratio of first geometric isomer to second geometric isomer which is at least 20-fold a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%. For example, a concentration ratio of 20:1 in a purified isomer would be 20-fold a concentration ratio of 1:1 in the mixture, and a concentration ratio of 5:1 (equivalent to 20:4) in a purified isomer would be 20-fold a concentration ratio of 1:4 in the mixture.

In some embodiments of any of the embodiments described herein, a purified first geometric isomer (according to any of the respective embodiments described herein) is characterized by a concentration ratio of first geometric isomer to second geometric isomer which is at least 30-fold a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%.

In some embodiments of any of the embodiments described herein, a purified first geometric isomer (according to any of the respective embodiments described herein) is characterized by a concentration ratio of first geometric isomer to second geometric isomer which is at least 50-fold a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%.

In some embodiments of any of the embodiments described herein, a purified first geometric isomer (according to any of the respective embodiments described herein) is characterized by a concentration ratio of first geometric isomer to second geometric isomer which is at least 100-fold a concentration ratio of the first geometric isomer to the second geometric isomer in the mixture of geometric isomers (according to any of the respective embodiments described herein). In some such embodiments, recovery of the isomer in the purified geometric isomer is at least 20%. In some embodiments, the recovery of the geometric isomer is at least 50%. In some embodiments, the recovery of the geometric isomer is at least 80%. In some embodiments, the recovery of the geometric isomer is at least 90%. In some such embodiments, the purified first geometric isomer is characterized by a purity of at least 90%. In some such embodiments, the purity is at least 95%. In some embodiments, the purity is at least 98%. In some embodiments, the purity is at least 99%. In some embodiments, the purity is at least 99.5%. In some embodiments, the purity is at least 99.8%. In some embodiments, the purity is at least 99.9%.

A purified geometric isomer obtained according to any of the respective embodiments described herein may optionally be an individual fraction obtained upon contacting a mixture with an ion exchange medium comprising silver ions, according to any of the respective embodiments described herein.

Alternatively, a purified geometric isomer obtained according to any of the respective embodiments described herein may optionally be a combination (e.g., mixture) of a plurality of fractions (comprising the geometric isomer) obtained upon contacting a mixture with an ion exchange medium comprising silver ions, according to any of the respective embodiments described herein.

In some embodiments of any of the embodiments described herein, the process further comprises selecting and/or combining a plurality of fractions (e.g., fractions obtained upon contacting a mixture with an ion exchange medium comprising silver ions according to any of the respective embodiments described herein) comprising the geometric isomer to thereby obtain the purified geometric isomer. In some such embodiments, each of the selected and/or combined fractions has a purity of the geometric isomer above a pre-determined level.

In some embodiments of any of the embodiments described herein, the process comprises selecting and/or combining fractions (e.g., fractions obtained upon contacting a mixture with an ion exchange medium comprising silver ions according to any of the respective embodiments described herein), wherein each of the fractions is characterized by a geometric isomer purity of at least 80%, to thereby obtain the purified geometric isomer. In some such embodiments, each of the fractions is characterized by a geometric isomer purity of at least 85%. In some embodiments, each of the fractions is characterized by a geometric isomer purity of at least 90%. In some embodiments, each of the fractions is characterized by a geometric isomer purity of at least 95%. In some embodiments, each of the fractions is characterized by a geometric isomer purity of at least 98%. In some embodiments, each of the fractions is characterized by a geometric isomer purity of at least 99%.

In some embodiments of any of the embodiments described herein, the process comprises selecting and/or combining fractions (e.g., fractions obtained upon contacting a mixture with an ion exchange medium comprising silver ions according to any of the respective embodiments described herein), wherein each of the fractions is characterized by a concentration ratio of first geometric isomer to second geometric isomer which is greater than a concentration ratio of the first geometric isomer to the second geometric isomer in the mixture of geometric isomers (according to any of the respective embodiments described herein). In some such embodiments, the concentration ratio of first geometric isomer to second geometric isomer is at least 120% of a concentration ratio of the first geometric isomer to the second geometric isomer in the mixture of geometric isomers. In some embodiments, the concentration ratio of first geometric isomer to second geometric isomer is at least 150% of a concentration ratio of the first geometric isomer to the second geometric isomer in the mixture of geometric isomers. In some embodiments, the concentration ratio of first geometric isomer to second geometric isomer is at least 200% of a concentration ratio of the first geometric isomer to the second geometric isomer in the mixture of geometric isomers.

In some embodiments, the concentration ratio of first geometric isomer to second geometric isomer is at least 300% of a concentration ratio of the first geometric isomer to the second geometric isomer in the mixture of geometric isomers.

In some embodiments, the concentration ratio of first geometric isomer to second geometric isomer is at least 500% of a concentration ratio of the first geometric isomer to the second geometric isomer in the mixture of geometric isomers.

In some embodiments, the concentration ratio of first geometric isomer to second geometric isomer is at least 1000% of (10-fold) a concentration ratio of the first geometric isomer to the second geometric isomer in the mixture of geometric isomers. In some embodiments, the concentration ratio of first geometric isomer to second geometric isomer is at least 20-fold a concentration ratio of the first geometric isomer to the second geometric isomer in the mixture of geometric isomers. In some embodiments, the concentration ratio of first geometric isomer to second geometric isomer is at least 30-fold a concentration ratio of the first geometric isomer to the second geometric isomer in the mixture of geometric isomers. In some embodiments, the concentration ratio of first geometric isomer to second geometric isomer is at least 50-fold a concentration ratio of the first geometric isomer to the second geometric isomer in the mixture of geometric isomers.

In some embodiments of any of the embodiments described herein, the mixture comprising geometric isomers of the unsaturated macrocyclic compound further comprises an additional compound in combination with the unsaturated macrocyclic compound (which may optionally be in a form of a single geometric isomer or a mixture of at least two geometric isomers), and the process comprises separating the additional compound from the unsaturated macrocyclic compound, for example, by contacting the mixture with an ion exchange medium comprising silver ions (e.g., according to any of the respective embodiments described herein).

Herein, the terms "additional "compound", is also referred to herein interchangeably, as "impurity" and describes a compound other than a geometric isomer of the unsaturated macrocyclic compound (or combination of geometric isomers thereof) in admixture with the unsaturated macrocyclic compound. The terms "additional compound" and "impurity" are not intended to imply a relative or absolute quantity of the compound.

In some embodiments, the additional compound is a compound which is structurally similar to the geometric isomer of the unsaturated macrocyclic compound. Examples of compounds structurally similar to an unsaturated macrocyclic compound include, without limitation, isomers (e.g., structural isomers) and saturated analogs of an unsaturated macrocyclic compound (e.g., as described in more detail in the following).

It is to be appreciated that an additional compound which may be undesirable in an admixture (e.g., with a desired geometric isomer of an unsaturated macrocyclic compound) may optionally be desirable in another context, for example, upon purification of the additional compound. For example, an unsaturated macrocyclic compound (according to some embodiments described herein) and an additional compound may optionally both be odoriferous compounds with different odors suitable for different products.

The additional compound may optionally comprise a different unsaturated macrocyclic compound, for example, wherein the additional compound is a structural isomer (as opposed to a geometric isomer) of the unsaturated macrocyclic compound, comprising an unsaturated bond at a different position from that of the abovementioned unsaturated macrocyclic compound.

Additional compound which are structural (not geometric) isomers may be present, for example, as an artifact of synthesis of the unsaturated macrocyclic compound, for example, in syntheses with incomplete control over the position of an unsaturated bond (e.g., resulting in unsaturated bonds at any of two adjacent positions); and/or may be difficult to separate from the unsaturated macrocyclic compound (e.g., due to strong structural similarities between the compounds).

Examples of mixtures of structural isomers known in the art, which may be separated according to some embodiments of the invention (e.g., as exemplified herein) include, without limitation, mixtures of oxacyclohexadec-12-en-1-one (e.g., (12E/Z)-oxacyclohexadec-12-en-1-one) and oxacyclohexadec-13-en-1-one (e.g., (13E/Z)-oxacyclohexadec-13-en-1-one)—e.g., a mixture which may be marketed under the tradename Globalide® or Habanolide®; and mixtures of 3-methyl-cyclopentadec-4-en-1-one (e.g., (4E/Z)-3-methyl-cyclopentadec-4-en-1-one) and 3-methyl-cyclopentadec-5-en-1-one (e.g., (5E/Z)-3-methyl-cyclopentadec-5-en-1-one)—e.g., a mixture which may be marketed under the tradename Muscenone®. Any one or more of the geometric isomers in such mixtures may optionally be purified, with purified (12E)-oxacyclohexadec-12-en-1-one and purified (5E)-3-methyl-cyclopentadec-5-en-1-one being non-limiting examples of particularly desirable purified isomers.

It is to be appreciated that when two or more different unsaturated macrocyclic compounds (i.e., which are not geometric isomers of one another) are present, a geometric isomer of any one or more of the unsaturated macrocyclic compounds may optionally be purified according to any of the respective embodiments described herein, wherein each of the unsaturated macrocyclic compounds is an "impurity" or "additional compound" with respect to another unsaturated macrocyclic compound.

Alternatively or additionally, the additional compound may comprise a saturated macrocyclic compound, for example, a saturated macrocyclic compound obtainable by saturation (e.g., hydrogenation) of the unsaturated macrocyclic compound. Such additional compounds may be present, for example, as an artifact of synthesis of the unsaturated macrocyclic compound, and/or may be difficult to separate from the unsaturated macrocyclic compound (e.g., due to strong structural similarities between the compounds).

In some embodiments of any of the respective embodiments described herein, a percentage of the additional compound (i.e., weight of the additional compound relative to the total weight of the additional compound and the geometric isomer being purified) in the purified geometric isomer is at least 25% less than a percentage of the additional compound (as defined hereinabove) in the mixture. In some such embodiments, a percentage of the additional compound (as defined hereinabove) in the purified geometric isomer is at least 50% less than a percentage of the additional compound (as defined hereinabove) in the mixture. In some such embodiments, a percentage of the additional compound in the purified geometric isomer is at least 70% less than a percentage of the additional compound in the mixture. In some such embodiments, a percentage of the additional compound in the purified geometric isomer is at least 80% less than a percentage of the additional compound in the mixture. In some such embodiments, a percentage of the additional compound in the purified geometric isomer is at least 90% less than a percentage of the additional compound in the mixture. In some such embodiments, a percentage of the additional compound in the purified geometric isomer is at least 95% less than a percentage of the additional compound in the mixture. In some such embodiments, a percentage of the additional compound in the purified geometric isomer is at least 98% less than a percentage of the additional compound in the mixture.

In some such embodiments, a percentage of the additional compound in the purified geometric isomer is at least 99% less than a percentage of the additional compound in the mixture.

According to an aspect of some embodiments of the invention, there is provided a purified macrocyclic compound (e.g., a purified geometric isomer of the macrocyclic compound) obtainable according to a process according to any of the respective embodiments described herein. The degree of purity and the type of compound of the purified macrocyclic compound may each independently be according to any of the respective embodiments described herein.

In some embodiments of any of the embodiments described herein, the obtainable purified macrocyclic compound (e.g., a purified geometric isomer of the macrocyclic compound) is characterized by a purity of at least 90% (according to any of the respective embodiments described herein). In some such embodiments, the purified macrocyclic compound is characterized by a purity of at least 95% (according to any of the respective embodiments described herein). In some such embodiments, the purified macrocyclic compound is characterized by a purity of at least 98% (according to any of the respective embodiments described herein). In some such embodiments, the purified macrocyclic compound is characterized by a purity of at least 99% (according to any of the respective embodiments described herein). In some such embodiments, the purified macrocyclic compound is characterized by a purity of at least 99.5% (according to any of the respective embodiments described herein). In some such embodiments, the purified macrocyclic compound is characterized by a purity of at least 99.8% (according to any of the respective embodiments described herein). In some such embodiments, the purified macrocyclic compound is characterized by a purity of at least 99.9% (according to any of the respective embodiments described herein).

System:

According to an aspect of some embodiments of the invention, there is provided a system configured for obtaining a purified geometric isomer of an unsaturated macrocyclic compound according to the process described herein, according to any of the respective embodiments described herein. The system, in some embodiments, comprises an ion exchange medium which comprises silver ions according to any of the embodiments described herein relating to an ion exchange medium comprising silver ions.

In some embodiments of any of the embodiments described herein, the ion exchange medium comprises a relatively high concentration of silver ions, according to any of the respective embodiments described herein.

For example, in some embodiments, at least 60% of the cations of the ion exchange medium are silver ions, and optionally at least 70%, optionally at least 80%, optionally at least 90%, and optionally at least 95% of the cations of the ion exchange medium are silver ions, according to any of the respective embodiments described herein.

Additionally or alternatively, in some embodiments, a concentration of silver ions in the ion exchange medium is at least 20%, at least 24%, at least 26%, at least 28%, at least 30%, at least 32%, and even at least 34%, by weight of the total dry weight of the ion exchange medium (including the weight of silver ions in the medium), according to any of the respective embodiments described herein.

Additionally or alternatively, in some embodiments, a concentration of silver ions in the ion exchange medium is at least 0.1 gram silver ions per $cm^3$ (e.g., from 0.1 to 0.3, from 0.1 to 0.2, or from 0.1 to 0.18 gram silver ions per $cm^3$), optionally at least 0.12 gram silver ions per $cm^3$ (e.g., from 0.12 to 0.3, from 0.12 to 0.2, or from 0.12 to 0.18 gram silver ions per $cm^3$), optionally at least 0.14 gram silver ions per $cm^3$ (e.g., from 0.14 to 0.3, from 0.14 to 0.2, or from 0.14 to 0.18 gram silver ions per $cm^3$), and optionally at least 0.16 gram silver ions per $cm^3$ (e.g., from 0.16 to 0.3, from 0.16 to 0.2, or from 0.16 to 0.18 gram silver ions per $cm^3$), according to any of the respective embodiments described herein.

In some embodiments, the system is configured for contacting the ion exchange medium with a solvent according to any of the respective embodiments described herein.

In some embodiments, the system is configured for effecting chromatography (e.g., according to any of the embodiments described herein relating to chromatography), for example, for effecting SMB chromatography according to any of the respective embodiments described herein.

As used herein the term "about" in the context of a temperature refers to ±5° C. In other context, the term "about" refers herein to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Macrocyclic compounds ((10E/Z)-oxacycloheptadec-10-en-2-one, (4Z)-cyclopentadec-4-en-1-one, (9Z)-cycloheptadec-9-en-1-one, (8E/Z)-cyclohexadec-8-en-1-one, (4E/Z)-3-methyl-cyclopentadec-4-en-1-one, (5E/Z)-3-methyl-cyclopentadec-5-en-1-one, (12E/Z)-oxacyclohexadec-12-en-2-one and (13E/Z)-oxacyclohexadec-13-en-2-one at the indicated E/Z ratios) were obtained from commercial vendors.

Ion exchange resin (PCR145K resin) was obtained from Purolite. The resin is a macroporous polystyrene (cross-linked with divinylbenzene) with sulfonic acid functional groups, and characterized by a capacity of 1.5 equivalents ($Na^+$) per liter and a particle size of 260-300 μm (according to manufacturer's specification).

Separation of Isomers of Macrocyclic Compounds (General Procedure):

Mixtures of E and Z isomers of macrocyclic compounds were prepared, and the isomer mixtures were separated using columns with ion exchange resin loaded with 1-100% silver ions (based on total amount of ions present in ion exchange resin).

Upon separation, a sequence of fractions was obtained, and the fractions were analyzed by gas chromatography (GC). The amount of each isomer in each fraction was quantified by calculating the area of the corresponding peak.

Purity and recovery were calculated as follows:

Subsets of sequential fractions were identified (e.g., all obtained fractions up to a particular point, or all obtained fractions from a particular point onwards), wherein the average purity in the subset of fractions was above or equal to a desired purity. Generally, the subset of fractions for an E isomer was distinct from the subset of fractions for a respective E isomer.

E isomer recovery was defined as the total amount of E isomer in all fractions where the average purity is ≥"desired purity", divided by the total amount E isomer in all fractions (×100%).

Z isomer recovery was defined as the total amount of Z isomer in all fractions where the average purity is ≥"desired purity", divided by the total amount Z isomer in all fractions (×100%).

Example 1

(10E)-Oxacycloheptadec-10-en-2-one Purification

In order to enrich an isomeric mixture with a desired isomer (E or Z), an isomerization process was used in some examples described herein.

Aluminum nitrate nonahydrate ($Al(NO_3)_3 \cdot 9H_2O$) was used for the isomerization. 1.0 gram (2.7 mmol) of aluminum nitrate nonahydrate and 50.0 grams (198.1 mmol) of (10Z)-oxacycloheptadec-10-en-2-one (94.9% isomeric purity)—or alternatively, (10E)-oxacycloheptadec-10-en-2-one (98.5% isomeric purity)—was heated under nitrogen with stirring at 109° C. for 45 minutes. The reaction mixture was cooled to room temperature. 10 grams of water was then added to 2.0 grams of the reaction mixture, and the mixture was shaken very intensively. The organic phase was separated by centrifugation at 5000 rotations per minute, and the separated organic phase was dissolved in dichloromethane and passed through a short silica gel column. The dichloromethane was evaporated by rotary evaporator. The organic phase had a ratio of E isomer to Z isomer of about 65:35, as determined by GC analysis.

These results indicate that isomerization can enrich a composition comprising an unsaturated macrocyclic compound in the desired isomer (E or Z), by obtaining a mixture of isomers at or near a thermodynamic equilibrium between the E and Z isomers (if the mixture is deficient in the desired isomer).

The mixture of E and Z isomers was then separated in accordance with the general procedures described hereinabove.

Specifically, 95 ml of PCR-145K resin was loaded with silver cations (silver cations being about 100% of the molar capacity of cations in resin, 34.5% by weight of the total weight of the resin, including weight of the silver ions) by an ion exchange process. After removing water from the resin, the loaded resin was placed in a laboratory glass separation column 1.1 cm in diameter and 100 cm in length (about 95 ml in volume).

0.2 gram of a mixture of (10E/Z)-oxacycloheptadec-10-en-2-one, in an E:Z ratio of 65:35, was injected into the column for separation. A mixture of methanol and water 70:30% (w/w) was used as the eluent, with the solvent flow rate was 3.8 ml/minute. The entire unit was contained in an enclosure maintained at constant temperature of 55° C. Fractions were collected by an R1 fraction collector, with a fraction sampling time of 1 minute. The fractions were analyzed by gas chromatography (GC). (10E)-Oxacycloheptadec-10-en-2-one was obtained with a recovery of 47.3%, at a purity of 96.0%.

In order to obtain a desired 98% purity of (10E)-oxacycloheptadec-10-en-2-one, 0.02 g of a mixture of (10E/Z)-oxacycloheptadec-10-en-2-one in an E:Z ratio of 80:20 was used for separation with same resin. Methanol was used as the eluent, and the solvent flow rate was 5.1 ml/minute. The entire unit was contained in an enclosure maintained at constant temperature of 55° C.

As shown in FIG. 1, (10E)-oxacycloheptadec-10-en-2-one and (10Z)-oxacycloheptadec-10-en-2-one eluted from the column at different times.

(10E)-Oxacycloheptadec-10-en-2-one was obtained with a recovery of 22.3%, at a purity of 98.2%.

Separation of 0.02 g of a mixture of (10E/Z)-oxacycloheptadec-10-en-2-one with an E:Z ratio of 80:20 was performed as described hereinabove, using a resin loaded with about 34.5% by weight (of the total weight of the resin) silver cations (about 100% of the molar capacity of cations in resin) and a mixture of methanol and water 70:30% (w/w) as the eluent (rather than methanol alone). The solvent flow rate was 3.0 ml/minute.

Figure 2:
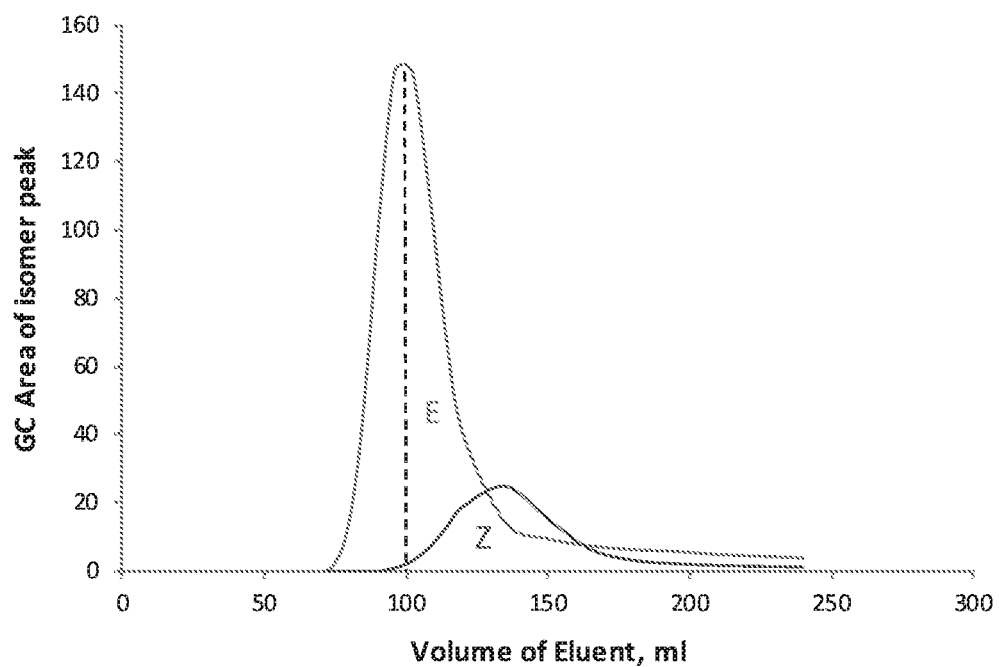
FIG. 2 is a graph showing amounts of E (high peak) and Z (low peak) isomers of oxacycloheptadec-10-en-2-one (as determined by gas chromatography (GC); arbitrary area units) eluted with a mixture of 70% methanol and 30% water (w/w) as solvent from a silver ion-loaded ion exchange column as a function of amount of solvent passed through the column (dashed line indicates maximum for E isomer).

As shown in FIG. 2, (10E)-oxacycloheptadec-10-en-2-one and (10Z)-oxacycloheptadec-10-en-2-one were separated to a greater degree when a 70:30% of methanol and water was used as eluent than when methanol was used as eluent (FIG. 1).

(10E)-Oxacycloheptadec-10-en-2-one was obtained with a recovery of 86.1%, at a purity of 97.6%.

The above results indicate that the use of a mixture of alcohol and water as eluent results in a more efficient recovery.

Example 2

Effect of Silver Ion Concentration on (10E)-oxacycloheptadec-10-en-2-one Purification Separation of 0.2 g of a mixture of (10E/Z)-oxacycloheptadec-10-en-2-one with an E:Z ratio of 80:20 was performed as described hereinabove in Example 1, but using a resin loaded with about 15% by weight (of the total weight of the resin) silver cations (about 43.5% of the molar capacity of cations in resin). A mixture of methanol and water 70:30% (w/w) was used as the eluent, and the solvent flow rate was 4.2 ml/minute. (10E)-Oxacycloheptadec-10-en-2-one was obtained with a recovery of 15.0%, at a purity of 91.7%.

These results indicate that high silver ion concentrations provide considerably more efficient separation.

Example 3

(10Z)-Oxacycloheptadec-10-en-2-one Purification 0.02 gram of a mixture of (10E/Z)-oxacycloheptadec-10-en-2-one, in an E:Z ratio of 19:81, was injected into the column, using equipment and procedures as described in Example 1 using a resin loaded with about 34.5% by weight (of the total weight of the resin) silver cations (about 100% of the molar capacity of cations in resin), except that the solvent flow rate was 5.7 ml/minute, and the temperature was 40° C.

(10Z)-Oxacycloheptadec-10-en-2-one was obtained with a recovery of 33.8%, at a purity of 93.4%.

Example 4

Separation of (10E)-oxacycloheptadec-10-en-2-one and (10Z)-oxacycloheptadec-10-en-2-one from oxacycloheptadecan-2-one 0.2 gram of a mixture of (10E)-oxacycloheptadec-10-en-2-one, (10Z)-oxacycloheptadec-10-en-2-one and oxacycloheptadecan-2-one (a.k.a. 16-hexadecanolide) at a ratio of 1:1:1 (w/w), was injected into the column for separation, using equipment and procedures as described in Example 1 (at a temperature of 55° C.) using a resin loaded with about 34.5% by weight (of the total weight of the resin) silver cations (about 100% of the molar capacity of cations in resin), except that the solvent flow rate was 4.2 ml/minute.

Figure 3:
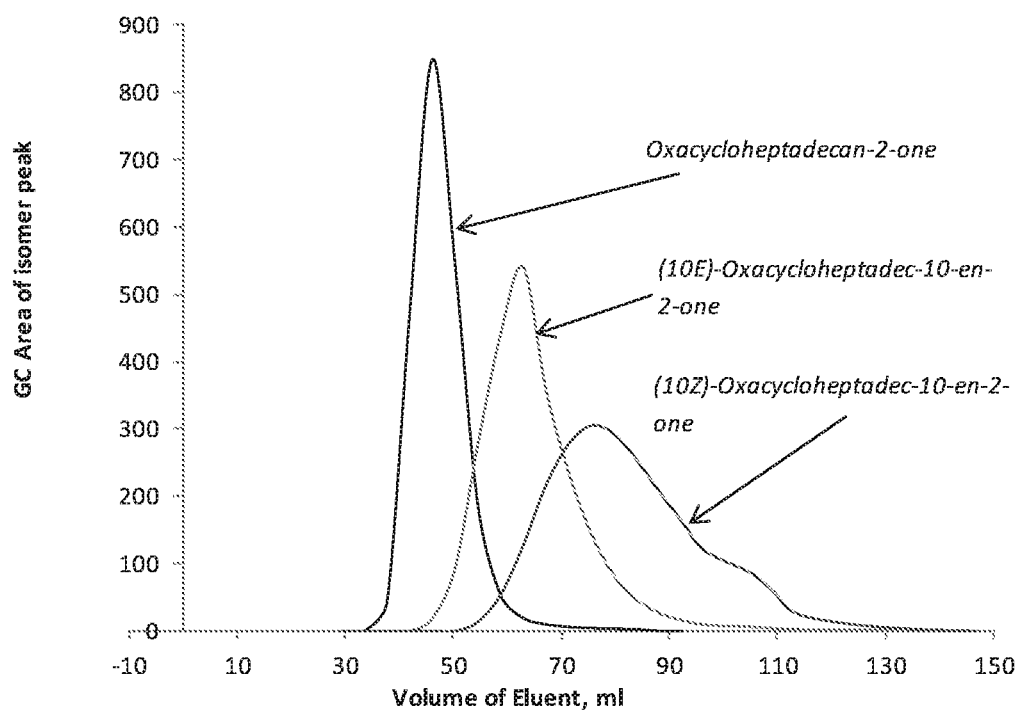
FIG. 3 is a graph showing amounts of oxacycloheptadecan-2-one and E and Z isomers of oxacycloheptadec-10-en-2-one (as determined by gas chromatography (GC); arbitrary area units) eluted from a silver ion-loaded ion exchange column as a function of amount of solvent passed through the column.

As shown in FIG. 3, oxacycloheptadecan-2-one, (10E)-oxacycloheptadec-10-en-2-one and (10Z)-oxacycloheptadec-10-en-2-one each eluted from the column at different times.

The purity of oxacycloheptadecan-2-one (defined as the amount of the oxacycloheptadecan-2-one divided by the total amount of oxacycloheptadecan-2-one and (10E/Z)-oxacycloheptadec-10-en-2-one) was 94.9%, and the recovery of oxacycloheptadecan-2-one was 86.9%.

These results indicate that structurally similar impurities can be separated from a desirable macrocyclic compound using procedures such as described herein.

Example 5

(4E)-Cyclopentadec-4-en-1-one and (4Z)-cyclopentadec-4-en-1-one Purification A mixture of (4E/Z)-cyclopentadec-4-en-1-one was prepared by subjecting (4Z)-cyclopentadec-4-en-1-one (96.4% isomeric purity) to isomerization with aluminum nitrate nonahydrate, using procedures similar to those described in Example 1.

80.9 milligrams (0.2 mmol) of aluminum nitrate nonahydrate and 2016.8 milligrams (9.1 mmol) of (4Z)-cyclopentadec-4-en-1-one were heated under nitrogen with stirring at 120° C. for 3 hours. The subsequent part of the workup is the same as described in Example 1. The obtained organic phase had a ratio of E isomer to Z isomer of about 78:22, as determined by GC analysis.

Separation of 0.02 g of a mixture of (4E/Z)-cyclopentadec-4-en-1-one with an E:Z ratio of 78:22 was performed as described hereinabove, using a resin loaded with about 15% by weight (of the total weight of the resin) silver cations (about 43.5% of the molar capacity of cations in resin). A mixture of methanol and water 70:30% (w/w) was used as the eluent, and the solvent flow rate was 3.0 ml/minute. The entire unit was contained in an enclosure maintained at constant temperature of 55° C. (4E)-Cyclopentadec-4-en-1-one was obtained with a recovery of 61.2%, at a purity of 90.9%.

In addition, separation of the same mixture of (4E/Z)-cyclopentadec-4-en-1-one was performed as described hereinabove, using a resin loaded with about 34.5% by weight (of the total weight of the resin) silver cations (about 100% of the molar capacity of cations in resin). A mixture of methanol and water 70:30% (w/w) was the eluent, with the solvent flow rate being 4.1 ml/minute. (4E)-Cyclopentadec-4-en-1-one was obtained with a recovery of 92.9%, at a purity of 98.3%.

Taken together, the above results indicate that high silver ion concentrations provide considerably more efficient separation, with higher purity and recovery.

In addition, separation of 0.02 g of a mixture of (4E)-cyclopentadec-4-en-1-one and (4Z)-cyclopentadec-4-en-1-one in ratio of 20:80 was performed as described hereinabove, using a resin loaded with about 34.5% by weight (of the total weight of the resin) silver cations (about 100% of the molar capacity of cations in resin) and a mixture of methanol and water 70:30% (w/w) as the eluent, with the solvent flow rate being 3.9 ml/minute. (4Z)-Cyclopentadec-4-en-1-one was obtained with a recovery of 71.7%, at a purity of 95.1%.

These results indicate that both the E and Z isomer of cyclopentadec-4-en-1-one can be purified efficiently, with high purity and recovery.

Example 6

(9E)-Cycloheptadec-9-en-1-one and (9Z)-cycloheptadec-9-en-1-one Purification

A mixture of (9E/Z)-cycloheptadec-9-en-1-one was prepared by subjecting (9Z)-cycloheptadec-9-en-1-one (90.4% isomeric purity) to isomerization with aluminum nitrate nonahydrate, using procedures similar to those described in Example 1.

82.0 milligrams (0.2 mmol) of aluminum nitrate nonahydrate and 2025.1 milligrams (8.1 mmol) of (9Z)-cycloheptadec-9-en-1-one were heated under nitrogen with stirring at 120° C. for 3 hours. The subsequent part of the workup is the same as described in Example 1. The obtained organic phase had a ratio of E isomer to Z isomer of about 71:29, as determined by GC analysis.

Purification of (9E)-cycloheptadec-9-en-1-one was performed as described hereinabove using a mixture of methanol and water 70:30% (w/w) as the eluent. 0.02 gram of a mixture of (9E/Z)-cycloheptadec-9-en-1-one, in an E:Z ratio of 71:29, was injected into a column for separation. The resin loaded with about 34.5% by weight (of the total weight of the resin) silver cations (about 100% of the molar capacity of cations in resin). The solvent flow rate was 3.0 ml/minute. The entire unit was contained in an enclosure maintained at constant temperature of 55° C. (9E)-Cycloheptadec-9-en-1-one was obtained with a recovery of 75.8%, at a purity of 97.3%.

A purification of (9Z)-cycloheptadec-9-en-1-one was performed by the similar procedure. 0.02 gram of a mixture of (9E/Z)-cycloheptadec-9-en-1-one, in an E:Z ratio of 23:77, was injected into a column for separation. The resin loaded with about 34.5% by weight (of the total weight of the resin) silver cations (about 100% of the molar capacity of cations in resin). The solvent flow rate was 3.6 ml/minute. (9Z)-Cycloheptadec-9-en-1-one was obtained with recovery 53.8%, at purity of 96.3%.

Example 7

(8E)-Cyclohexadec-8-en-1-one and (8Z)-cyclohexadec-8-en-1-one Purification 0.3 gram of a mixture of (8E/Z)-cyclohexadec-8-en-1-one in an E:Z ratio of 67:33 (as received), was injected into a column for separation, using equipment and procedures as described in Example 1. A mixture of methanol and water 70:30% (w/w) was used as the eluent. The resin was loaded with about 34.5% by weight (of the total weight of the resin) silver cations (about 100% of the molar capacity of cations in resin). The solvent flow rate was 4.0 ml/minute. The entire unit was contained in an enclosure maintained at constant temperature of 55° C.

(8E)-Cyclohexadec-8-en-1-one was obtained with a recovery of 72.1%, at a purity of 98.8%.

Purification of (8Z)-cyclohexadec-8-en-1-one was performed by a similar procedure. 0.02 gram of a mixture of (8E/Z)-cyclohexadec-8-en-1-one, in an E:Z ratio of 15:85, was injected into a column for separation. The resin loaded with about 34.5% by weight (of the total weight of the resin) silver cations (about 100% of the molar capacity of cations in resin). The solvent flow rate was 3.8 ml/minute.

(8Z)-Cyclohexadec-8-en-1-one was obtained with recovery 68.8%, at purity of 98.5%.

Example 8

Purification of (4E)-3-methyl-cyclopentadec-4-en-1-one, (4Z)-3-methyl-cyclopentadec-4-en-1-one, (5E)-3-methyl-cyclopentadec-5-en-1-one and (5Z)-3-methyl-cyclopentadec-5-en-1-one 0.02 gram of a mixture of (4E/Z)-3-methyl-cyclopentadec-4-en-1-one and (5E/Z)-3-methyl-cyclopentadec-5-en-1-one, in a 4E:5E:4Z:5Z ratio of 13.3:37.2:3.5:46.0 (as received), was injected into a column for separation, using equipment and procedures as described in Example 1. A mixture of methanol and water 70:30% (w/w) was used as the eluent. The resin was loaded with about 34.5% by weight (of the total weight of the resin) silver cations (about 100% of the molar capacity of cations in resin). The solvent flow rate was 1.1 ml/minute. The entire unit was contained in an enclosure maintained at constant temperature of 55° C.

(4E)-3-Methyl-cyclopentadec-4-en-1-one was obtained with a recovery of 33.5%, at a purity of 90.9%.

(5E)-3-Methyl-cyclopentadec-5-en-1-one was obtained with a recovery of 70.1%, at a purity of 82.7%.

(4Z)-3-Methyl-cyclopentadec-4-en-1-one was obtained with a recovery of 69.9%, at a purity of 11.8%.

(5Z)-3-Methyl-cyclopentadec-5-en-1-one was obtained with a recovery of 82.4%, at a purity of 81.0%.

Example 9

Purification of (12E)-oxacyclohexadec-12-en-2-one, (12Z)-oxacyclohexadec-12-en-2-one, (13E)-oxacyclohexadec-13-en-2-one and (13Z)-oxacyclohexadec-13-en-2-one 0.02 gram of a mixture of (12E/Z)-oxacyclohexadec-12-en-2-one and (13E/Z)-oxacyclohexadec-13-en-2-one, in relative proportions (as received) of 44.39% (12E)-oxacyclohexadec-12-en-2-one, 29.77% (13E)-oxacyclohexadec-13-en-2-one, and 25.84% mixture of (12Z)-oxacyclohexadec-12-en-2-one and (13Z)-oxacyclohexadec-13-en-2-one, was injected into a column for separation, using equipment and procedures as described in Example 1. A mixture of methanol and water 70:30% (w/w) was used as the eluent. The resin was loaded with about 34.5% by weight (of the total weight of the resin) silver cations (about 100% of the molar capacity of cations in resin). The solvent flow rate was 1.0 ml/minute. The entire unit was contained in an enclosure maintained at constant temperature of 55° C.

(12E)-Oxacyclohexadec-12-en-2-one was obtained with a recovery of 64.5%, at a purity of 75.2%.

(13E)-Oxacyclohexadec-13-en-2-one was obtained with a recovery of 59.2%, at a purity of 96.3%.

A mixture of (12Z)-oxacyclohexadec-12-en-2-one and (13Z)-oxacyclohexadec-13-en-2-one was obtained with a recovery of 42.8%, at a purity of 60.9%.

Example 10

Simulated moving bed (SMB) continuous separation of (10E)-oxacycloheptadec-10-en-2-one and (10Z)-oxacycloheptadec-10-en-2-one A SMB (simulated moving bed) continuous chromatographic separation system was used for separation of E and Z isomers of (10E/Z)-oxacycloheptadec-10-en-2-one. The system contained a set of 16 columns affixed to a rotating platform and a central rotary valve which provides one port per column, that accepts inlet and outlet process streams. Each column was 2.5 cm in diameter and 54 cm in length and contained about 265 ml of PCR-145K resin loaded with silver cations (e.g., as described hereinabove).

The separation temperature was about 20° C. The desorption process of E and Z isomers of (10E/Z)-oxacycloheptadec-10-en-2-one was slower at lower temperature, which resulted in poorer separation (data not shown).

A mixture of (10E/10Z)-oxacycloheptadec-10-en-2-one in an E:Z ratio of about 80:20 was continuously fed to the system at a flow rate of 0.125 ml/minute. Eluent downstream was 73 ml/minute, extract downstream was 39.4 ml/minute, raffinate downstream was 11.2 ml/minute, and purge stream was 125 ml/minute. The columns rotated with an 8 minutes set step. The fractions obtained by the continuous chromatographic separation are summarized in Table 1.

As shown in Table 1, (10E)-oxacycloheptadec-10-en-2-one was obtained at an isomeric purity of 92.5% and at a recovery of 47.7%.

TABLE 1

Results of simulated moving bed continuous chromatographic separation of (10E/Z)-oxacycloheptadec-10-en-2-one

| Stream Type | E-isomer purity (%) | Z-isomer purity (%) | E-isomer recovery (%) | Z-isomer recovery (%) |
|---|---|---|---|---|
| Feed stream | 80.2 | 19.8 | — | — |
| Extract stream | 92.5 | 7.5 | 47.7 | 19.1 |
| Raffinate stream | 78.0 | 22.0 | 0.7 | 0.8 |
| Purge steam | 72.2 | 27.8 | 51.6 | 80.1 |

The above results demonstrate feasibility of the process. The process is performed at a separation temperature of 50-55° C. (rather than about 20° C.) in order to obtain better separation.

Example 11

Additional Simulated Moving Bed (SMB) Continuous Separations

A SMB (simulated moving bed) continuous chromatographic separator system is used according to procedures similar to those described hereinabove in Example 10. The system contains a set of 8-25 columns (e.g., 16 columns) affixed to a rotating platform and a central rotary valve which provides 8-25 fixed ports (e.g., one port per column) that accept inlet and outlet process streams. Each column is 1.0-5.0 cm in diameter and 50-150 cm in length (optionally 2.5 cm in diameter and 54 cm in length) and contains 100-500 ml (optionally about 265 ml) of PCR-145K resin loaded with silver cations (e.g., as described hereinabove). The entire system is maintained at a constant temperature in a range of about 35-60° C. (e.g., 55-60° C.).

A feeds stream of mixture of E/Z is continuously fed to port (designated "feed"). A recycle stream is optionally withdrawn from extract, raffinate and/or purge ports, and combined with a solvent stream to form an elution stream.

The E or Z isomer product is obtained at an isomeric purity of at least 90-95% and at a yield of at least 20%, preferably at least 40%, of the total amount of E and Z isomers fed to the system.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A process of obtaining a purified geometric isomer of an unsaturated macrocyclic compound, said unsaturated macrocyclic compound comprising a ring of at least 12 atoms, the process comprising contacting an ion exchange medium comprising silver ions with a mixture comprising at least one geometric isomer of the unsaturated macrocyclic compound, to thereby obtain at least one fraction comprising said purified geometric isomer of said macrocyclic compound, wherein:

said contacting said ion exchange medium with said mixture is effected at a temperature in a range of from 30° C. to 80° C.; and/or said contacting said ion exchange medium with said mixture is effected at a first temperature, and the process further comprises eluting said at least one fraction from said ion exchange medium at a second temperature in a range of from 30° C. to 80° C., said second temperature being higher than said first temperature, wherein said unsaturated macrocyclic compound is selected from the group consisting of a cycloalkenone and an oxacycloalkenone.

2. The process of claim 1, wherein said purified geometric isomer is characterized by a purity of at least 90%.

3. The process of claim 1, wherein said mixture comprises a first geometric isomer and a second geometric isomer of said unsaturated macrocyclic compound, and the process comprises separating said first geometric isomer and said second geometric isomer, said purified geometric isomer being a purified first geometric isomer.

4. The process of claim 1, wherein said mixture comprises an additional compound in combination with said unsaturated macrocyclic compound, and the process comprises separating said additional compound from said unsaturated macrocyclic compound.

5. The process of claim 1, wherein at least 60% of the cations of said ion exchange medium are silver ions.

6. The process of claim 1, wherein a concentration of silver ions in said ion exchange medium is at least 20% by weight of the total dry weight of said ion exchange medium.

7. The process of claim 1, wherein a concentration of silver ions in said ion exchange medium is in a range of from 0.1 to 0.3 grams silver ions per $cm^3$.

8. The process of claim 1, wherein said ion exchange medium comprises cross-linked polystyrene substituted with sulfonic acid groups or a salt thereof.

9. The process of claim 1, further comprising contacting said ion exchange medium comprising silver ions with an alcoholic and/or aqueous solvent.

10. The process of claim 9, wherein said solvent comprises methanol and/or ethanol.

11. The process of claim 9, wherein a concentration of water in said solvent is in a range of from 0 to 40 weight percent.

12. The process of claim 9, wherein said solvent is contacted with said ion exchange medium such that it flows through the ion exchange medium at a rate in a range of from 1 to 10 bed volumes per hour.

13. The process of claim 9, wherein said solvent is contacted with said ion exchange medium such that it flows through the ion exchange medium at a rate in a range of from 2.5 to 250 cm per minute.

14. The process of claim 1, wherein said contacting said ion exchange medium with said mixture is effected at a temperature in a range of from 30° C. to 80° C.

15. The process of claim 1, wherein said contacting said ion exchange medium with said mixture is effected at said first temperature, and the process further comprises eluting said at least one fraction from said ion exchange medium at said second temperature.

16. The process of claim 1, comprising:
contacting said ion exchange medium comprising silver ions with said mixture comprising at least one geometric isomer of the unsaturated macrocyclic compound, to thereby obtain at least one first fraction comprising said purified geometric isomer, and at least one second fraction comprising said geometric isomer at a purity which is lower than a purity of said geometric isomer in said mixture; and
contacting an ion exchange medium comprising silver ions with said at least one second fraction, to thereby obtain at least one third fraction comprising said purified geometric isomer.

17. The process of claim 1, comprising isomerizing at least a portion of said unsaturated macrocyclic compound in a first mixture to obtain a second mixture having a different isomeric purity than that of said first mixture, and contacting said ion exchange medium comprising silver ions with said second mixture.

18. The process of claim 17, wherein said isomerizing is effected by contact with an aluminum salt at a temperature of at least 80° C.

19. The process of claim 18, wherein said isomerizing is effected by contact with aluminum nitrate.

20. The process of claim 1, wherein said unsaturated macrocyclic compound comprises a ring of at least 13 atoms.

21. The process of claim 20, wherein said unsaturated macrocyclic compound comprises a ring of at least 14 atoms.

22. The process of claim 1, wherein said oxacycloalkenone is a lactone (1-oxacycloalken-2-one).

23. The process of claim 22, wherein said cycloalkenone is selected from the group consisting of a cyclotetradecenone, a cyclopentadecenone, a cyclohexadecenone, and a cycloheptadecenone, and said lactone is selected from the group consisting of an oxacyclotetradecen-2-one, an oxacyclopentadecen-2-one, an oxacyclohexadecen-2-one, and an oxacycloheptadecen-2-one.

24. The process of claim 1, wherein said unsaturated macrocyclic compound comprises a single carbon-carbon double bond, and said geometric isomers comprise the cis isomer and the trans isomer.

25. The process of claim 1, wherein said unsaturated macrocyclic compound is selected from the group consisting of an odoriferous compound, an antibiotic compound, an antiviral compound, an anti-parasitic agent, an anti-proliferative agent, an immune-modulating compound, and an antifungal compound.

* * * * *